US009427324B1

(12) United States Patent
Wensel

(10) Patent No.: US 9,427,324 B1
(45) Date of Patent: Aug. 30, 2016

(54) INTERVERTEBRAL FUSION DEVICE AND METHOD OF USE

(75) Inventor: Jeffrey Paris Wensel, Eugene, OR (US)

(73) Assignee: SPINELOGIK, INC., Eugene, OR (US)

( * ) Notice: Subject to any disclaimer, the term of this patent is extended or adjusted under 35 U.S.C. 154(b) by 20 days.

(21) Appl. No.: 13/032,634

(22) Filed: Feb. 22, 2011

Related U.S. Application Data

(60) Provisional application No. 61/306,943, filed on Feb. 22, 2010.

(51) Int. Cl.
*A61F 2/44* (2006.01)

(52) U.S. Cl.
CPC ............... *A61F 2/44* (2013.01); *A61F 2/447* (2013.01); *A61F 2002/448* (2013.01)

(58) Field of Classification Search
CPC ............ A61F 2/4455; A61F 2/4611; A61F 2220/0025; A61F 2220/0033; A61F 2002/4475; A61F 2002/4627; A61F 2002/4624; A61F 2017/0256; A61B 2017/2923; A61B 2017/2943
USPC ...... 606/86 A, 86 R, 246, 248–249, 99–100; 623/17.11–17.16
See application file for complete search history.

(56) References Cited

U.S. PATENT DOCUMENTS

| | | | |
|---|---|---|---|
| 776,049 A | 11/1904 | Frühling | |
| 4,554,914 A | 11/1985 | Kapp et al. | |
| 4,653,489 A | 3/1987 | Tronzo | |
| 4,904,260 A | 2/1990 | Ray et al. | |
| D312,309 S | 11/1990 | Michelson | |
| 5,015,247 A | 5/1991 | Michelson | |
| 5,314,477 A | 5/1994 | Marnay | |
| 5,397,364 A * | 3/1995 | Kozak et al. | 623/17.11 |
| 5,484,437 A | 1/1996 | Michelson | |
| 5,505,732 A | 4/1996 | Michelson | |
| 5,522,817 A | 6/1996 | Sander et al. | |
| 5,522,899 A | 6/1996 | Michelson | |
| D377,095 S | 12/1996 | Michelson | |
| D377,096 S | 12/1996 | Michelson | |
| D377,527 S | 1/1997 | Michelson | |
| 5,593,409 A | 1/1997 | Michelson | |
| 5,609,635 A | 3/1997 | Michelson | |
| 5,609,636 A | 3/1997 | Kohrs et al. | |
| 5,653,761 A | 8/1997 | Pisharodi | |

(Continued)

FOREIGN PATENT DOCUMENTS

| | | |
|---|---|---|
| DE | 19944681 | 3/2001 |
| RU | 2004218 | 12/1993 |

OTHER PUBLICATIONS

Updated portions of prosecution history of U.S. Appl. No. 12/113,362, filed Nov. 10, 2011, Wensel, Jeffrey Paris.

(Continued)

*Primary Examiner* — Todd E Manahan
*Assistant Examiner* — Jessica Weiss
(74) *Attorney, Agent, or Firm* — Adeli LLP

(57) ABSTRACT

Some embodiments of the invention provide an apparatus that (1) delivers a fusion member between two vertebral bodies after at least a portion of the fibrocartilaginous disc between the vertebral bodies has been removed, and (2) affixes the fusion member to the vertebral bodies. In some embodiments, the apparatus includes (1) a fusion member that is delivered and positioned between the vertebral bodies, (2) a delivery member that delivers and positions the fusion member between the vertebral bodies.

22 Claims, 24 Drawing Sheets

(56) References Cited

U.S. PATENT DOCUMENTS

| | | | |
|---|---|---|---|
| 5,702,391 A | 12/1997 | Lin | |
| D392,387 S | 3/1998 | Michelson | |
| 5,741,253 A | 4/1998 | Michelson | |
| 5,766,254 A | 6/1998 | Gelbard | |
| 5,772,661 A | 6/1998 | Michelson | |
| 5,776,199 A | 7/1998 | Michelson | |
| 5,785,710 A | 7/1998 | Michelson | |
| 5,797,909 A | 8/1998 | Michelson | |
| 5,860,973 A | 1/1999 | Michelson | |
| D425,989 S | 5/2000 | Michelson | |
| 6,056,749 A | 5/2000 | Kuslich | |
| 6,080,155 A | 6/2000 | Michelson | |
| 6,096,038 A | 8/2000 | Michelson | |
| 6,120,502 A | 9/2000 | Michelson | |
| 6,120,503 A | 9/2000 | Michelson | |
| 6,123,705 A | 9/2000 | Michelson | |
| 6,136,001 A | 10/2000 | Michelson | |
| 6,139,551 A | 10/2000 | Michelson | |
| 6,149,650 A | 11/2000 | Michelson | |
| RE37,005 E | 12/2000 | Michelson | |
| 6,159,215 A | 12/2000 | Urbahns et al. | |
| 6,190,388 B1 | 2/2001 | Michelson | |
| 6,210,412 B1 | 4/2001 | Michelson | |
| RE37,161 E | 5/2001 | Michelson | |
| 6,224,595 B1 | 5/2001 | Michelson | |
| 6,224,607 B1 | 5/2001 | Michelson | |
| 6,241,770 B1 | 6/2001 | Michelson | |
| 6,264,656 B1 | 7/2001 | Michelson | |
| 6,270,498 B1 | 8/2001 | Michelson | |
| 6,302,914 B1 | 10/2001 | Michelson | |
| 6,315,795 B1* | 11/2001 | Scarborough et al. | 623/17.11 |
| 6,350,283 B1 | 2/2002 | Michelson | |
| 6,436,098 B1 | 8/2002 | Michelson | |
| 6,447,544 B1 | 9/2002 | Michelson | |
| 6,447,546 B1 | 9/2002 | Bramlet et al. | |
| 6,447,547 B1 | 9/2002 | Michelson | |
| 6,468,276 B1* | 10/2002 | McKay | 606/86 A |
| 6,478,823 B1 | 11/2002 | Michelson | |
| 6,485,517 B1 | 11/2002 | Michelson | |
| 6,500,205 B1 | 12/2002 | Michelson | |
| 6,537,320 B1 | 3/2003 | Michelson | |
| 6,554,836 B2 | 4/2003 | Michelson | |
| 6,558,423 B1 | 5/2003 | Michelson | |
| 6,565,574 B2 | 5/2003 | Michelson | |
| 6,582,432 B1 | 6/2003 | Michelson | |
| 6,605,089 B1 | 8/2003 | Michelson | |
| 6,652,584 B2 | 11/2003 | Michelson | |
| 6,666,890 B2 | 12/2003 | Michelson | |
| 6,709,458 B2 | 3/2004 | Michelson | |
| 6,716,247 B2 | 4/2004 | Michelson | |
| 6,730,127 B2 | 5/2004 | Michelson | |
| 6,733,535 B2 | 5/2004 | Michelson | |
| 6,749,636 B2 | 6/2004 | Michelson | |
| 6,758,849 B1 | 7/2004 | Michelson | |
| 6,767,366 B2* | 7/2004 | Lee et al. | 623/17.16 |
| 6,767,367 B1 | 7/2004 | Michelson | |
| 6,770,074 B2 | 8/2004 | Michelson | |
| 6,793,679 B2 | 9/2004 | Michelson | |
| 6,808,537 B2 | 10/2004 | Michelson | |
| 6,814,756 B1 | 11/2004 | Michelson | |
| 6,827,740 B1 | 12/2004 | Michelson | |
| 6,849,093 B2 | 2/2005 | Michelson | |
| 6,875,213 B2 | 4/2005 | Michelson | |
| 6,890,355 B2 | 5/2005 | Michelson | |
| 6,902,578 B1* | 6/2005 | Anderson et al. | 623/16.11 |
| 6,923,810 B1 | 8/2005 | Michelson | |
| 6,923,830 B2 | 8/2005 | Michelson | |
| 6,946,000 B2 | 9/2005 | Senegas et al. | |
| 6,962,606 B2 | 11/2005 | Michelson | |
| 6,972,019 B2 | 12/2005 | Michelson | |
| 6,972,035 B2 | 12/2005 | Michelson | |
| 6,981,975 B2 | 1/2006 | Michelson | |
| 6,989,031 B2 | 1/2006 | Michelson | |
| 7,008,453 B1 | 3/2006 | Michelson | |
| 7,022,137 B2 | 4/2006 | Michelson | |
| 7,033,394 B2 | 4/2006 | Michelson | |
| 7,041,135 B2 | 5/2006 | Michelson | |
| 7,051,417 B2 | 5/2006 | Michelson | |
| 7,056,342 B2 | 6/2006 | Michelson | |
| 7,063,701 B2 | 6/2006 | Michelson | |
| 7,063,702 B2 | 6/2006 | Michelson | |
| 7,066,961 B2 | 6/2006 | Michelson | |
| 7,094,239 B1 | 8/2006 | Michelson | |
| 7,112,206 B2 | 9/2006 | Michelson | |
| 7,115,128 B2 | 10/2006 | Michelson | |
| 7,115,143 B1 | 10/2006 | Michelson | |
| 7,118,579 B2 | 10/2006 | Michelson | |
| 7,118,598 B2 | 10/2006 | Michelson | |
| 7,128,760 B2 | 10/2006 | Michelson | |
| 7,156,875 B2 | 1/2007 | Michelson | |
| 7,163,561 B2 | 1/2007 | Michelson | |
| 7,166,107 B2 | 1/2007 | Anderson | |
| 7,166,129 B2 | 1/2007 | Michelson | |
| 7,195,643 B2* | 3/2007 | Jackson | 623/17.11 |
| 7,207,991 B2 | 4/2007 | Michelson | |
| 7,244,275 B2 | 7/2007 | Michelson | |
| 7,255,698 B2 | 8/2007 | Michelson | |
| 7,255,713 B2 | 8/2007 | Malek | |
| 7,264,622 B2 | 9/2007 | Michelson | |
| 7,288,093 B2 | 10/2007 | Michelson | |
| 7,291,149 B1 | 11/2007 | Michelson | |
| 7,320,686 B2 | 1/2008 | Serhan et al. | |
| 7,326,214 B2 | 2/2008 | Michelson | |
| 7,326,248 B2 | 2/2008 | Michelson | |
| 7,354,442 B2 | 4/2008 | Sasso et al. | |
| 7,387,643 B2 | 6/2008 | Michelson | |
| 7,396,365 B2 | 7/2008 | Michelson | |
| 7,399,303 B2 | 7/2008 | Michelson | |
| 7,410,501 B2 | 8/2008 | Michelson | |
| 7,431,722 B1 | 10/2008 | Michelson | |
| 7,435,262 B2 | 10/2008 | Michelson | |
| 7,442,209 B2 | 10/2008 | Michelson | |
| 7,445,636 B2 | 11/2008 | Michelson | |
| 7,452,359 B1 | 11/2008 | Michelson | |
| 7,455,672 B2 | 11/2008 | Michelson | |
| 7,455,692 B2 | 11/2008 | Michelson | |
| 7,462,195 B1 | 12/2008 | Michelson | |
| 7,491,205 B1 | 2/2009 | Michelson | |
| 7,497,859 B2 | 3/2009 | Zucherman et al. | |
| 7,503,933 B2 | 3/2009 | Michelson | |
| 7,534,254 B1 | 5/2009 | Michelson | |
| 7,540,882 B2 | 6/2009 | Michelson | |
| 7,569,054 B2 | 8/2009 | Michelson | |
| 7,608,107 B2 | 10/2009 | Michelson | |
| 7,611,536 B2 | 11/2009 | Michelson | |
| 7,618,423 B1 | 11/2009 | Valentine et al. | |
| 7,637,951 B2 | 12/2009 | Michelson | |
| 7,637,954 B2 | 12/2009 | Michelson | |
| 7,655,027 B2 | 2/2010 | Michelson | |
| 7,662,184 B2* | 2/2010 | Edwards et al. | 623/17.11 |
| 7,686,805 B2 | 3/2010 | Michelson | |
| 7,691,148 B2 | 4/2010 | Michelson | |
| 7,717,947 B1 | 5/2010 | Wilberg et al. | |
| 7,722,619 B2 | 5/2010 | Michelson | |
| 7,771,475 B2 | 8/2010 | Michelson | |
| 7,789,914 B2 | 9/2010 | Michelson | |
| 7,794,502 B2 | 9/2010 | Michelson | |
| 7,815,683 B2 | 10/2010 | Melkent et al. | |
| 7,828,800 B2 | 11/2010 | Michelson | |
| 7,833,271 B2 | 11/2010 | Mitchell et al. | |
| 7,887,565 B2 | 2/2011 | Michelson | |
| 7,892,286 B2 | 2/2011 | Michelson | |
| 7,914,530 B2 | 3/2011 | Michelson | |
| 7,914,554 B2 | 3/2011 | Michelson | |
| 7,922,729 B2 | 4/2011 | Michelson | |
| 7,931,840 B2 | 4/2011 | Michelson | |
| 7,935,116 B2 | 5/2011 | Michelson | |
| 7,935,149 B2 | 5/2011 | Michelson | |
| 7,942,933 B2 | 5/2011 | Michelson | |
| 7,959,675 B2 | 6/2011 | Gately | |
| 7,972,365 B2 | 7/2011 | Michelson | |
| 7,972,381 B2 | 7/2011 | Michelson | |
| 7,976,566 B2 | 7/2011 | Michelson | |
| 8,083,744 B2 | 12/2011 | Dorchak et al. | |

(56) References Cited

U.S. PATENT DOCUMENTS

| | | | |
|---|---|---|---|
| 8,167,915 | B2 | 5/2012 | Ferree et al. |
| 8,182,532 | B2 | 5/2012 | Anderson et al. |
| 8,182,539 | B2 | 5/2012 | Tyber et al. |
| 8,206,449 | B2 | 6/2012 | Jansen et al. |
| 8,231,676 | B2 | 7/2012 | Trudeau et al. |
| 8,241,364 | B2 | 8/2012 | Hansell et al. |
| 8,292,960 | B2 | 10/2012 | Kleiner |
| 8,308,805 | B2 | 11/2012 | Lynn et al. |
| 8,313,528 | B1 | 11/2012 | Wensel |
| 8,333,804 | B1 | 12/2012 | Wensel |
| 8,366,774 | B1 | 2/2013 | Bruffey et al. |
| 8,372,126 | B2 | 2/2013 | Trieu et al. |
| 8,382,808 | B2 | 2/2013 | Wilberg et al. |
| 8,382,839 | B1 | 2/2013 | Wensel |
| 8,454,623 | B2 | 6/2013 | Patel et al. |
| 8,460,385 | B1 | 6/2013 | Wensel |
| 8,523,945 | B1 | 9/2013 | Wensel |
| 8,551,175 | B1 | 10/2013 | Wensel |
| 8,685,104 | B2 | 4/2014 | Lee et al. |
| 8,906,101 | B2 | 12/2014 | Lee et al. |
| 9,028,549 | B1 | 5/2015 | Wensel |
| 2002/0099378 | A1 | 7/2002 | Michelson |
| 2003/0187436 | A1 | 10/2003 | Bolger et al. |
| 2003/0191371 | A1 | 10/2003 | Smith et al. |
| 2004/0010316 | A1 | 1/2004 | William et al. |
| 2005/0010294 | A1 | 1/2005 | Michelson |
| 2005/0065519 | A1* | 3/2005 | Michelson .................. 606/61 |
| 2005/0065607 | A1* | 3/2005 | Gross .................. 623/17.11 |
| 2005/0070913 | A1 | 3/2005 | Milbocker et al. |
| 2005/0137707 | A1 | 6/2005 | Malek |
| 2005/0251257 | A1 | 11/2005 | Mitchell et al. |
| 2005/0277930 | A1 | 12/2005 | Parsons |
| 2005/0283246 | A1 | 12/2005 | Cauthen, III et al. |
| 2006/0009850 | A1 | 1/2006 | Frigg et al. |
| 2006/0036322 | A1 | 2/2006 | Reiley |
| 2006/0058876 | A1* | 3/2006 | McKinley .................. 623/17.11 |
| 2006/0079961 | A1 | 4/2006 | Michelson |
| 2006/0089646 | A1 | 4/2006 | Bonutti |
| 2006/0095136 | A1 | 5/2006 | McLuen |
| 2006/0106460 | A1 | 5/2006 | Messerli et al. |
| 2006/0122623 | A1 | 6/2006 | Truckai et al. |
| 2006/0206207 | A1* | 9/2006 | Dryer et al. .................. 623/17.11 |
| 2007/0038219 | A1 | 2/2007 | Matthis et al. |
| 2007/0043441 | A1 | 2/2007 | Pisharodi |
| 2007/0050030 | A1 | 3/2007 | Kim |
| 2007/0055376 | A1* | 3/2007 | Michelson .................. 623/17.11 |
| 2007/0219635 | A1 | 9/2007 | Mathieu et al. |
| 2007/0225813 | A1 | 9/2007 | Haines |
| 2007/0270858 | A1 | 11/2007 | Trieu et al. |
| 2007/0276377 | A1 | 11/2007 | Yundt |
| 2008/0015694 | A1 | 1/2008 | Tribus |
| 2008/0065215 | A1 | 3/2008 | Reiley |
| 2008/0091200 | A1 | 4/2008 | Kuiper et al. |
| 2008/0091205 | A1 | 4/2008 | Kuiper et al. |
| 2008/0221695 | A1* | 9/2008 | Jacofsky et al. .................. 623/17.16 |
| 2008/0269901 | A1 | 10/2008 | Baynham et al. |
| 2008/0281428 | A1 | 11/2008 | Meyers et al. |
| 2008/0319481 | A1 | 12/2008 | Moore |
| 2009/0138015 | A1 | 5/2009 | Conner et al. |
| 2009/0149959 | A1 | 6/2009 | Conner et al. |
| 2009/0164020 | A1 | 6/2009 | Janowski et al. |
| 2009/0171389 | A1 | 7/2009 | Sankaran |
| 2009/0171461 | A1 | 7/2009 | Conner et al. |
| 2009/0234392 | A1 | 9/2009 | Dziedzic et al. |
| 2009/0265007 | A1 | 10/2009 | Colleran |
| 2009/0292316 | A1 | 11/2009 | Hess |
| 2010/0114317 | A1 | 5/2010 | Lambrecht et al. |
| 2010/0160984 | A1 | 6/2010 | Berry et al. |
| 2010/0168861 | A1 | 7/2010 | Yundt |
| 2010/0204796 | A1 | 8/2010 | Bae et al. |
| 2010/0249935 | A1 | 9/2010 | Slivka et al. |
| 2010/0268339 | A1 | 10/2010 | Malinin et al. |
| 2010/0286777 | A1 | 11/2010 | Errico et al. |
| 2011/0166660 | A1 | 7/2011 | Laurence |
| 2011/0196494 | A1 | 8/2011 | Yedlicka et al. |
| 2011/0208311 | A1 | 8/2011 | Janowski |
| 2012/0078373 | A1 | 3/2012 | Gamache et al. |
| 2012/0095561 | A1 | 4/2012 | Voisard et al. |
| 2012/0191191 | A1 | 7/2012 | Trieu |
| 2012/0330426 | A1 | 12/2012 | McLaughlin et al. |
| 2013/0030536 | A1 | 1/2013 | Rhoda et al. |
| 2014/0088711 | A1 | 3/2014 | Chin et al. |
| 2014/0180417 | A1 | 6/2014 | Bergey |

OTHER PUBLICATIONS

Updated portions of prosecution history of U.S. Appl. No. 12/361,525, filed Oct. 4, 2011, Wensel, Jeffrey Paris.
Updated portions of prosecution history of U.S. Appl. No. 12/383,950, filed Oct. 28, 2011, Wensel, Jeffrey Paris.
U.S. Appl. No. 60/916,414, filed May 7, 2007.
Updated portions of prosecution history of U.S. Appl. No. 12/361,525, filed Jun. 14, 2012, Wensel, Jeffrey Paris.
Updated portions of prosecution history of U.S. Appl. No. 12/705,972, filed May 14, 2012, Wensel, Jeffrey Paris.
Updated portions of prosecution history of U.S. Appl. No. 12/383,950, filed Jun. 20, 2012, Wensel, Jeffrey Paris.
Updated portions of prosecution history of U.S. Appl. No. 12/705,974, filed Jun. 19, 2012, Wensel, Jeffrey Paris.
Updated portions of prosecution history of U.S. Appl. No. 12/113,362, filed Jul. 12, 2012, Wensel, Jeffrey Paris.
Updated portions of prosecution history of U.S. Appl. No. 12/361,525, filed Jul. 3, 2012, Wensel, Jeffrey Paris.
Updated portions of prosecution history of U.S. Appl. No. 12/705,970, filed Jul. 11, 2012, Wensel, Jeffrey Paris.
Updated portions of prosecution history of U.S. Appl. No. 12/705,974, filed Jul. 20, 2012, Wensel, Jeffrey Paris.
Updated portions of prosecution history of U.S. Appl. No. 12/705,978, filed Jul. 3, 2012, Wensel, Jeffrey Paris.
U.S. Appl. No. 12/113,362, filed May 1, 2008, Wensel, Jeffrey Paris.
U.S. Appl. No. 12/361,525, filed Jan. 28, 2009, Wensel, Jeffrey Paris.
U.S. Appl. No. 12/383,950, filed Mar. 27, 2009, Wensel, Jeffrey Paris.
U.S. Appl. No. 12/705,970, filed Feb. 15, 2010, Wensel, Jeffrey Paris.
U.S. Appl. No. 12/705,972, filed Feb. 15, 2010, Wensel, Jeffrey Paris.
U.S. Appl. No. 12/705,974, filed Feb. 15, 2010, Wensel, Jeffrey Paris.
U.S. Appl. No. 12/705,978, filed Feb. 15, 2010, Wensel, Jeffrey Paris.
Portions of prosecution history of U.S. Appl. No. 12/113,362, filed Mar. 28, 2011, Wensel, Jeffrey Paris.
Portions of prosecution history of U.S. Appl. No. 12/361,525, filed Jul. 8, 2011, Wensel, Jeffrey Paris.
Portions of prosecution history of U.S. Appl. No. 12/383,950, filed Jul. 21, 2011, Wensel, Jeffrey Paris.
Portions of prosecution history of U.S. Appl. No. 12/705,970, filed Jul. 27, 2010, Wensel, Jeffrey Paris.
Portions of prosecution history of U.S. Appl. No. 12/705,972, filed Jul. 27, 2010, Wensel, Jeffrey Paris.
Portions of prosecution history of U.S. Appl. No. 12/705,974, filed Jul. 27, 2010, Wensel, Jeffrey Paris.
Portions of prosecution history of U.S. Appl. No. 12/705,978, filed Jul. 27, 2010, Wensel, Jeffrey Paris.
Updated portions of prosecution history of U.S. Appl. No. 12/113,362, filed Oct. 17, 2012, Wensel, Jeffrey Paris.
Updated portions of prosecution history of U.S. Appl. No. 12/361,525, filed Oct. 3, 2012, Wensel, Jeffrey Paris.
Updated portions of prosecution history of U.S. Appl. No. 12/383,950, filed Oct. 12, 2012, Wensel, Jeffrey Paris.
Updated portions of prosecution history of U.S. Appl. No. 12/705,970, filed Oct. 11, 2012, Wensel, Jeffrey Paris.
Updated portions of prosecution history of U.S. Appl. No. 12/705,972, filed Oct. 4, 2012, Wensel, Jeffrey Paris.
Updated portions of prosecution history of U.S. Appl. No. 12/705,974, filed Oct. 10, 2012, Wensel, Jeffrey Paris.
Updated portions of prosecution history of U.S. Appl. No.

(56) References Cited

OTHER PUBLICATIONS

12/705,978, filed Oct. 3, 2012, Wensel, Jeffrey Paris.
Updated portions of prosecution history of U.S. Appl. No. 12/113,362, filed Apr. 19, 2012, Wensel, Jeffrey Paris.
Updated portions of prosecution history of U.S. Appl. No. 12/361,525, filed Feb. 14, 2012, Wensel, Jeffrey Paris.
Updated portions of prosecution history of U.S. Appl. No. 12/705,970, filed Mar. 22, 2012, Wensel, Jeffrey Paris.
Updated portions of prosecution history of U.S. Appl. No. 12/705,972, filed Apr. 12, 2012, Wensel, Jeffrey Paris.
Updated portions of prosecution history of U.S. Appl. No. 12/705,978, filed Mar. 22, 2012, Wensel, Jeffrey Paris.
U.S. Appl. No. 60/989,100, filed Nov. 19, 2007.
U.S. Appl. No. 13/753,373, filed Jan. 29, 2013, Wensel, Jeffrey Paris.
Updated portions of prosecution history of U.S. Appl. No. 12/705,970, filed Mar. 19, 2013, Wensel, Jeffrey Paris.
Updated portions of prosecution history of U.S. Appl. No. 12/705,972, filed Jan. 30, 2013, Wensel, Jeffrey Paris.
U.S. Appl. No. 13/909,039, filed Jun. 3, 2013, Wensel, Jeffrey Paris.
Updated portions of prosecution history of U.S. Appl. No. 12/705,970, filed Apr. 17, 2013, Wensel, Jeffrey Paris.
Updated portions of prosecution history of U.S. Appl. No. 12/705,972, filed May 15, 2013, Wensel, Jeffrey Paris.
Updated portions of prosecution history of U.S. Appl. No. 12/705,974, filed May 9, 2013, Wensel, Jeffrey Paris.
Updated portions of prosecution history of U.S. Appl. No. 12/705,978, filed May 28, 2013, Wensel, Jeffrey Paris.
U.S. Appl. No. 13/655,412, filed Oct. 18, 2012, Wensel, Jeffrey Paris.
U.S. Appl. No. 13/663,472, filed Oct. 30, 2012, Wensel, Jeffrey Paris.
Portions of prosecution history of U.S. Appl. No. 13/663,472, Jan. 16, 2013, Wensel, Jeffrey Paris.
Updated portions of prosecution history of U.S. Appl. No. 12/361,525, filed Nov. 14, 2012, Wensel, Jeffrey Paris.
Portions of prosecution history of U.S. Appl. No. 13/655,412, filed Jan. 16, 2013, Wensel, Jeffrey Paris.
Updated portions of prosecution history of U.S. Appl. No. 12/383,950, filed Jan. 14, 2013, Wensel, Jeffrey Paris.
Updated portions of prosecution history of U.S. Appl. No. 12/705,970, filed Dec. 13, 2012, Wensel, Jeffrey Paris.
Updated portions of prosecution history of U.S. Appl. No. 12/705,972, filed Dec. 17, 2012, Wensel, Jeffrey Paris.
Updated portions of prosecution history of U.S. Appl. No. 12/705,974, filed Dec. 17, 2012, Wensel, Jeffrey Paris.
Updated portions of prosecution history of U.S. Appl. No. 12/705,978, filed Jan. 17, 2013, Wensel, Jeffrey Paris.
Updated portions of prosecution history of U.S. Appl. No. 12/705,970, filed Aug. 5, 2013, Wensel, Jeffrey Paris.
Updated portions of prosecution history of U.S. Appl. No. 12/705,974, Sep. 13, 2013, Wensel, Jeffrey Paris.
Updated portions of prosecution history of U.S. Appl. No. 12/705,978, filed Dec. 27, 2013, Wensel, Jeffrey Paris.
Portions of prosecution history of U.S. Appl. No. 13/753,373, filed Apr. 25, 2014, Wensel, Jeffrey Paris.
Portions of prosecution history of U.S. Appl. No. 13/663,472, filed Apr. 14, 2014, Wensel, Jeffrey Paris.
Portions of prosecution history of U.S. Appl. No. 13/909,039, filed Apr. 25, 2014, Wensel, Jeffrey Paris.
Updated portions of prosecution history of U.S. Appl. No. 13/663,472, filed Oct. 20, 2014, Spinelogik, Inc.
Updated portions of prosecution history of U.S. Appl. No. 13/655,412, filed Nov. 18, 2014, Spinelogik, Inc.
Updated portions of prosecution history of U.S. Appl. No. 13/753,373, filed Dec. 4, 2014, Spinelogik, Inc.
Updated portions of prosecution history of U.S. Appl. No. 13/909,039, filed Dec. 4, 2014, Spinelogik, Inc.
Updated portions of prosecution history of U.S. Appl. No. 13/655,412, filed Dec. 19, 2014, Wensel, Jeffrey Paris.
Updated portions of prosecution history of U.S. Appl. No. 13/753,373, filed Dec. 26, 2014, Wensel, Jeffrey Paris.
Updated portions of prosecution history of U.S. Appl. No. 13/909,039, filed Jan. 5, 2015, Wensel, Jeffrey Paris.
Updated portions of prosecution history of U.S. Appl. No. 13/663,472, filed Apr. 3, 2015, Wensel, Jeffrey Paris.
Updated portions of prosecution history of U.S. Appl. No. 13/655,412, filed Apr. 20, 2015, Wensel, Jeffrey Paris.
Updated portions of prosecution history of U.S. Appl. No. 13/753,373, filed Apr. 3, 2015, Wensel, Jeffrey Paris.
Updated portions of prosecution history of U.S. Appl. No. 13/909,039, filed May 5, 2015, Wensel, Jeffrey Paris.

* cited by examiner

INTERVERTEBRAL FUSION DEVICE AND METHOD OF USE

CLAIM OF BENEFIT TO PRIOR APPLICATION

This application claims the benefit of U.S. Provisional Patent Application 61/306,943, filed on Feb. 22, 2010. The above-mentioned United States Provisional Patent Application is incorporated herein by reference.

FIELD OF THE INVENTION

The invention pertains to spinal implants and surgical procedures for spinal fusion and stabilization.

BACKGROUND OF THE INVENTION

Back and neck pain are the leading causes of disability and lost productivity for American workers under the age of 45. Degenerative disc disease and its sequelae, whereby the fibrocartilaginous disc between adjacent vertebral bodies loses height, hydration and structural integrity, is one of the most common causes of back and neck pain and may develop secondary to traumatic injuries, inflammatory processes or various degenerative disorders. When conservative treatment fails, surgical fusion of the vertebral segments across the abnormal disc may be the only currently available procedure for pain relief. An increasing number of these spinal fusions are performed each year. It is estimated that over half a million of these procedures were performed in the United States last year alone.

Various surgical approaches to abnormal lumbar disc spaces are employed and include anterior interbody fusions, posterior interbody fusions and tranforaminal fusions. At cervical levels, an anterior approach is often employed. These procedures may be augmented by various posterior element instrumentation techniques. Regardless of the surgical approach, the goal is to achieve solid bony fusion between the involved endplates and eliminate the symptoms caused by motion and associated degenerative and other reactive changes between these unstable vertebral segments.

The first lumbar fusion procedures involved removal of a portion of the abnormal disc and placement of autologous bone graft material in the disc space without other instrumentation in the vertebral bodies or posterior elements. This approach often failed due to inadequate structural integrity. Subsequently, cortical bone dowels and femoral ring allografts were employed in an attempt to restore disc space height and augment structural integrity. After U.S. Pat. No. 4,961,740 ("Ray, et al.") introduced the concept of the threaded cylindrical interbody fusion cage in 1990, numerous other interbody fusion devices were developed. These devices include cylindrical, rectangular, and tapered cages and spacers composed of metals, polymers, human bone allograft and other materials. Some of these devices incorporate or are coated with human bone morphogenetic protein or other agents to promote new bone formation and accelerate fusion. Despite these advancements, failure rates for spinal fusion surgeries remain unacceptably high, greater than 10 percent in most series.

Therefore, there is a need in the art for an improved method to effect a more rapid, reliable fusion between unstable vertebral segments and avoid the considerable medical and economic impact of failed spinal fusions.

SUMMARY OF THE INVENTION

Some embodiments of the invention provide an apparatus that (1) delivers a fusion member between two vertebral bodies after at least a portion of the fibrocartilaginous disc between the vertebral bodies has been removed, and (2) affixes the fusion member to the vertebral bodies. In some embodiments, the apparatus includes (1) a fusion member that is delivered and positioned between the vertebral bodies, (2) a delivery member that delivers and positions the fusion member between the vertebral bodies.

In some embodiments, the interbody fusion member is a shaped block (e.g., a rectangular or oblong block) with one or more channels. As mentioned above, this member is placed between endplates of adjacent vertebrae following a partial or complete discectomy. In this position, two or more sides of the fusion member are in contact with the opposed endplates. These contacting sides in some embodiments restore both disc height and physiologic lordosis. In some embodiments, these sides are parallel to each other, whereas in other embodiments, these sides are nonparallel such that the fusion member presents a tapered profile when viewed laterally.

In some embodiments, a delivery member delivers the fusion member between vertebral bodies and a retention mechanism couples the delivery member to the fusion member. In some embodiments, the delivery member has retention teeth that mate with retention grooves of the fusion member. The delivery member, retention grooves, and retention teeth form the retention mechanism of some embodiments. Other embodiments might have different retention mechanisms. For instance, in some embodiments, the retention teeth are on the fusion member while the retention grooves are on the delivery member. Moreover, instead of, or in conjunction with, this tooth and groove approach, one of ordinary skill will realize that other embodiments use other retention structures (e.g., other male/female structures, other structures such as expandable clasps that encapsulate the lateral edges of the fusion member, other structures such as a clamp, etc.) to affix the delivery member to the fusion member.

The retention mechanism is used in some embodiments as a way of controllably detaching the delivery member from the fusion member after the medical practitioner determines that the fusion member is placed at the desired position between two vertebral bodies. When the medical practitioner determines (e.g., by viewing x-ray images of the patient) that the fusion member is not placed at an appropriate position between two vertebral bodies, the medical practitioner can use the delivery member to reposition the fusion member to the desired location. One of ordinary skill will realize that the delivery member and/or retention mechanism of some embodiments can be used for delivery of any type of interbody fusion members between two vertebral bodies (e.g., even those that utilize anchoring members to further anchor the fusion members to the vertebral bodies). Once the fusion member is in place, the delivery member may be removed, as mentioned above.

To enhance the structural integrity of the coupling between the fusion device and the vertebral bodies, some embodiments define various surface contours along the fusion member's surface. Examples of such contours include angled teeth and backfacing ridges. These contours (e.g., angled teeth and backfacing ridge) allow the fusion member to be inserted between vertebral bodies but prevent the fusion member from being easily withdrawn from between the vertebral bodies.

BRIEF DESCRIPTION OF THE DRAWINGS

The novel features of the invention are set forth in the appended claims. However, for purpose of explanation, several embodiments of the invention are set forth in the following figures.

DETAILED DESCRIPTION OF THE INVENTION

Figure 1:
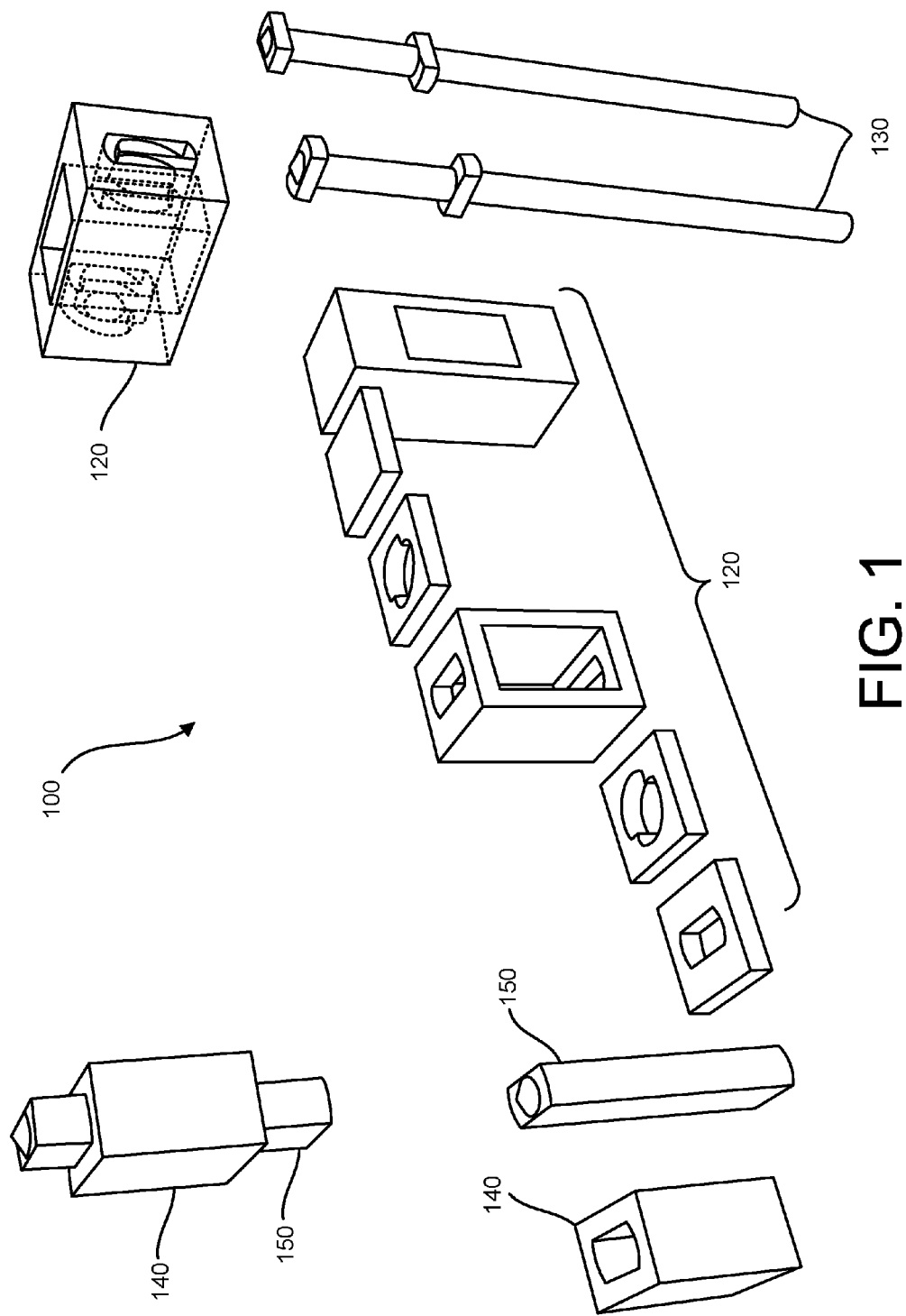
FIGS. 1-4 provide different perspectives of an exploded view of the apparatus.
Figure 2:
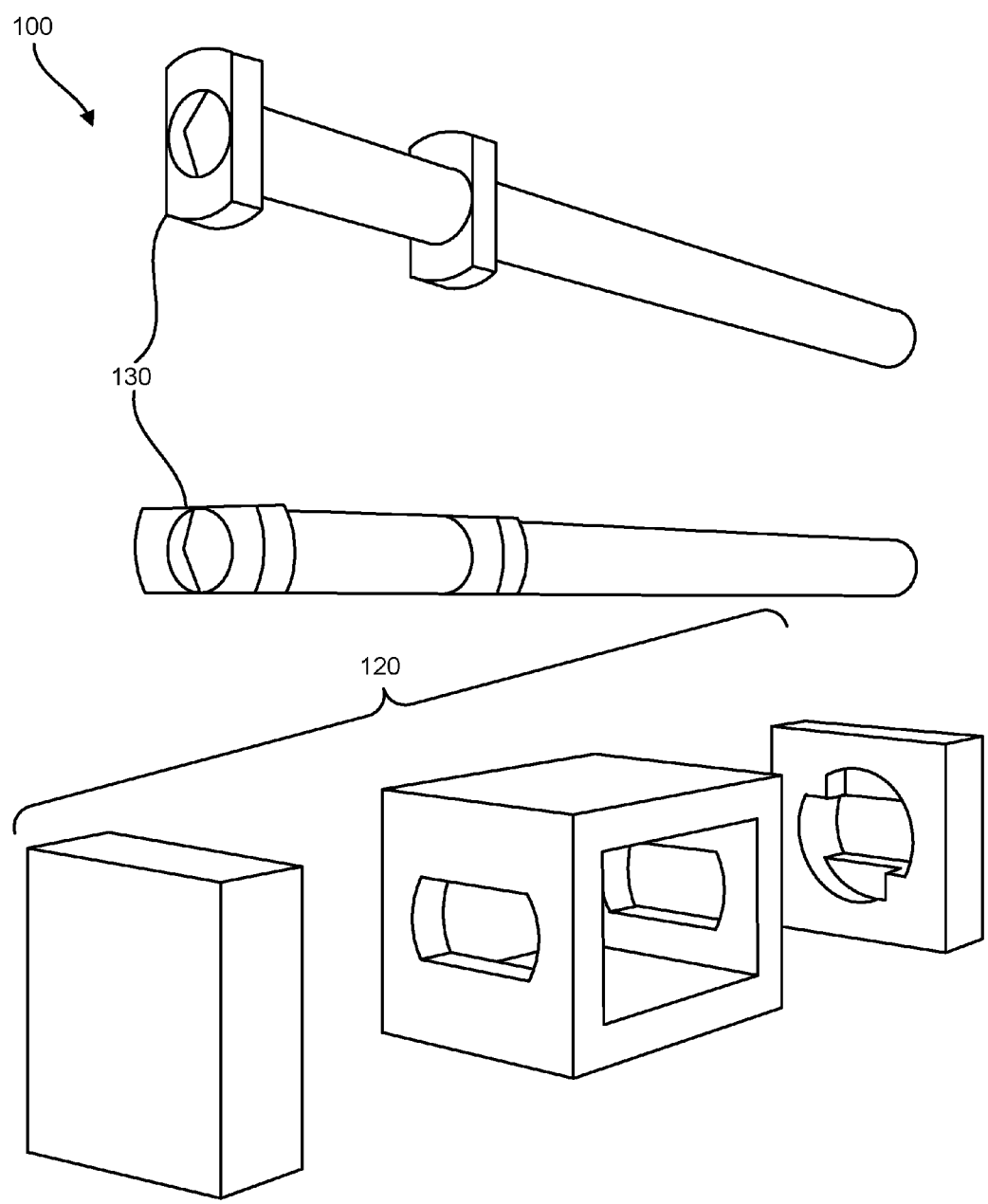
Figure 3:
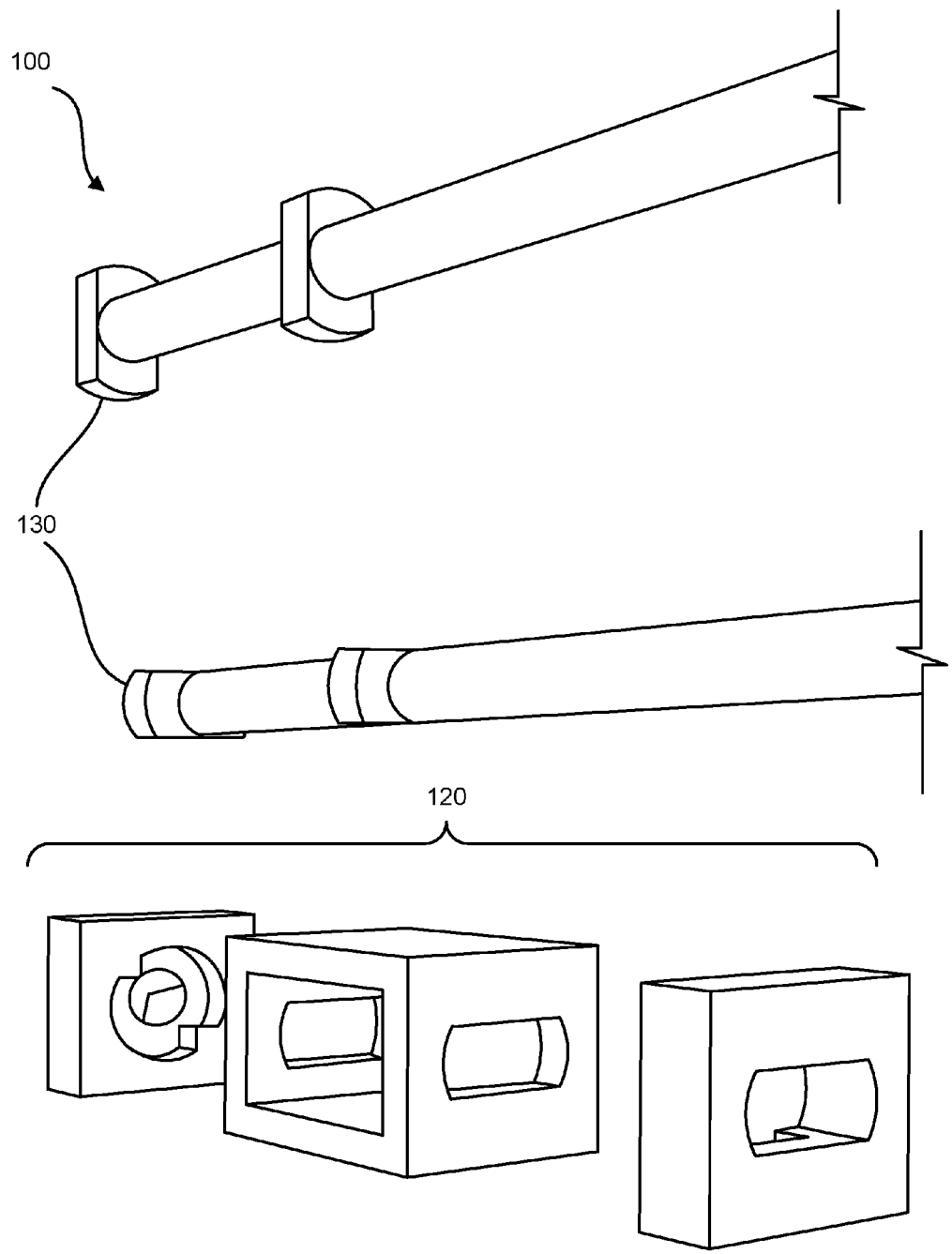
Figure 4:
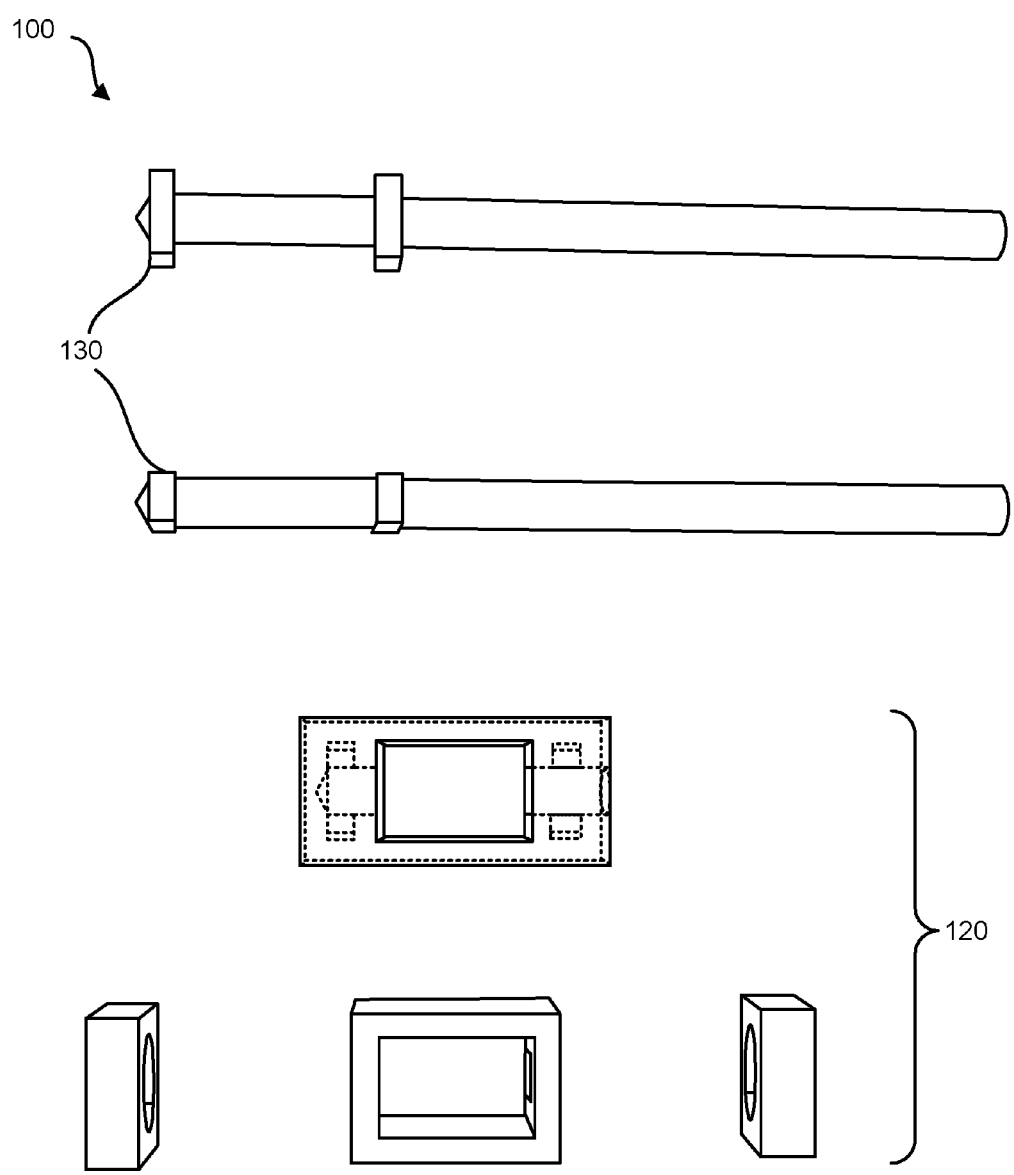

In the following description, numerous details are set forth to provide a better understanding of the various embodiments of the invention. However, one of reasonable skill in the art will realize that the invention may be practiced without the use of the specific details presented herein. In some instances of describing the invention, well-known structures may be omitted or shown in block diagram form to avoid obscuring the description of the invention with unnecessary detail. Therefore, the examples provided herein for description and clarification should not be interpreted as in any way limiting the language of the claims.

Some embodiments of the invention provide an apparatus that (1) delivers a fusion member between two vertebral bodies after at least a portion of the fibrocartilaginous disc between the vertebral bodies has been removed, and (2) affixes the fusion member to the vertebral bodies. In some embodiments, the apparatus includes (1) a fusion member that is delivered and positioned between the vertebral bodies and (2) a delivery member that delivers and positions the fusion member between the vertebral bodies.

In some embodiments, the interbody fusion member is a shaped block (e.g., a rectangular or oblong block) with one or more channels (e.g., tubular channels). As mentioned above, this member is placed between endplates of adjacent vertebrae following a partial or complete discectomy. In this position, two or more sides of the fusion member are in contact with the opposed endplates. These contacting sides may be parallel to each other, or nonparallel such that the fusion member presents a tapered profile when viewed laterally so as to restore both disc height and physiologic lordosis.

In some embodiments, a delivery member delivers the fusion member between vertebral bodies and a retention mechanism couples the delivery member to the fusion member. In some embodiments, the delivery member has retention teeth that mate with retention grooves of the fusion member. The delivery member, retention teeth, and retention grooves of the fusion member form the retention mechanism of some embodiments. Other embodiments might have different retention mechanisms. For instance, in some embodiments, the retention teeth are on the fusion member while the retention grooves are on the delivery member. Moreover, instead of, or in conjunction with, this tooth and groove approach, one of ordinary skill will realize that other embodiments use other retention structures (e.g., other male/female structures, other structures such as expandable clasps that encapsulate the lateral edges of the fusion member, other structures such as a clamp, etc.) to affix the delivery member to the fusion member.

The retention mechanism is used in some embodiments as a way of controllably detaching the delivery member from the fusion member after the medical practitioner (1) determines that the fusion member is placed at the desired position between two vertebral bodies. When the medical practitioner determines (e.g., by viewing x-ray images of the patient) that the fusion member is not placed at an appropriate position between two vertebral bodies, he can use the delivery member to reposition the fusion member to the desired location. One of ordinary skill will realize that the delivery member and/or retention mechanism of some embodiments can be used for delivery of any type of interbody fusion members between two vertebral bodies (e.g., even those that utilize anchoring members and/or PMMA or bone cement to further anchor the fusion members to the vertebral bodies). Once the fusion member is in place, the delivery member may be removed, as mentioned above.

To enhance the structural integrity of the coupling between the fusion device and the vertebral bodies, some embodiments define various surface contours along the fusion member's surface. Examples of such contours include angled teeth and backfacing ridges. These contours (e.g., angled teeth and backfacing ridge) allow the fusion member to be inserted between vertebral bodies but prevent the fusion member from being easily withdrawn from between the vertebral bodies.

To better understand these embodiments, it is helpful to understand relevant terminology and describe examples of the invention in use. Therefore, the following sections present relevant terminology, and provide an overview of an exemplary fusion procedure of some embodiments and of a number of more specific design features and variations.

I. Definitions and Terminology

The spinal column of humans and other vertebrates comprises vertebral bodies and posterior osseous elements that provide structural support and also serve to protect the spinal cord and other spinal canal contents. The vertebral bodies are the cylindrical segmental osseous structures that form the anterior margin of the spinal canal and are separated from each other by fibrocartilaginous intervertebral discs. In the present discussion, the term "fusion member" refers to a device positioned between vertebral bodies. In some embodiments, the fusion member has one or more channels for the passage of delivery members and/or the retention and positioning of bone graft material or bone graft substitutes between adjacent vertebral bodies.

II. Components of the Fusion Apparatus

Some embodiments of the invention provide an apparatus that (1) delivers a fusion member between two vertebral bodies after at least a portion of the fibrocartilaginous disc between the vertebral bodies has been removed, and (2) affixes the fusion member to the vertebral bodies.

Figure 5:
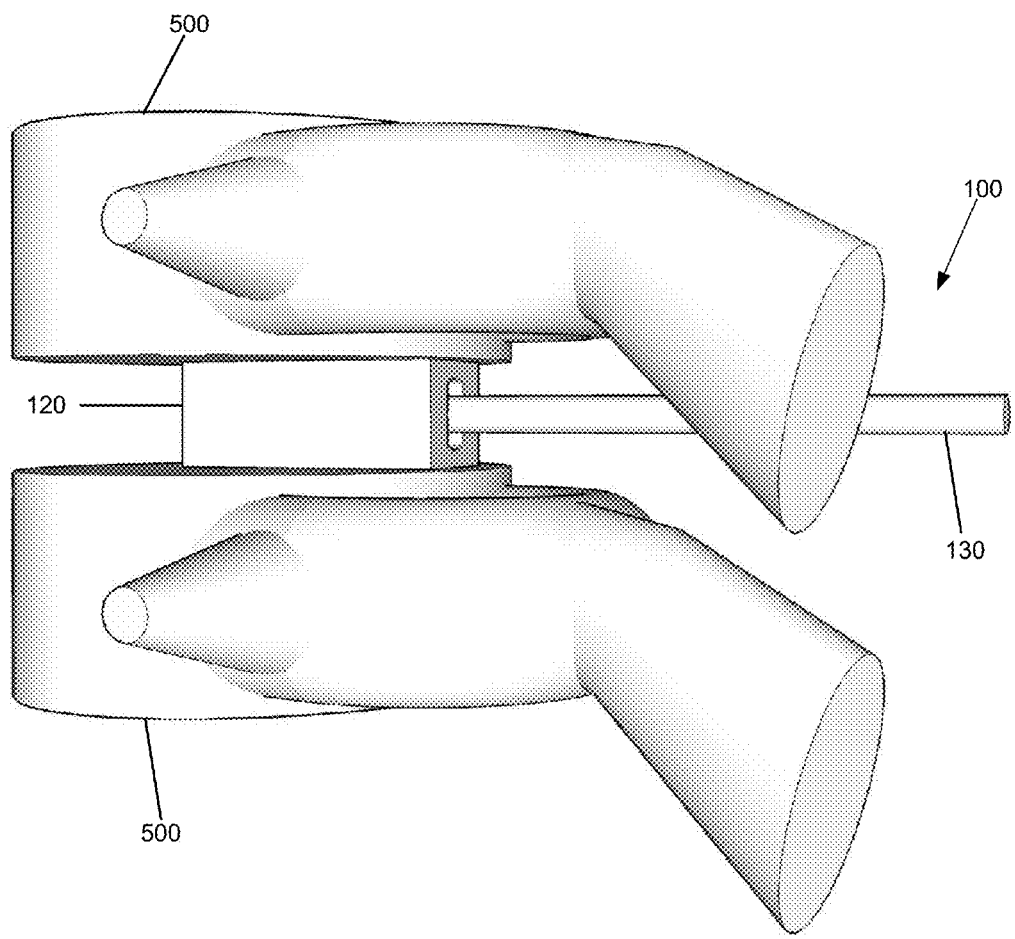
FIG. 5-6 provide different perspectives of the assembled apparatus in relation to two vertebral bodies between which a fusion member is placed.
Figure 6:
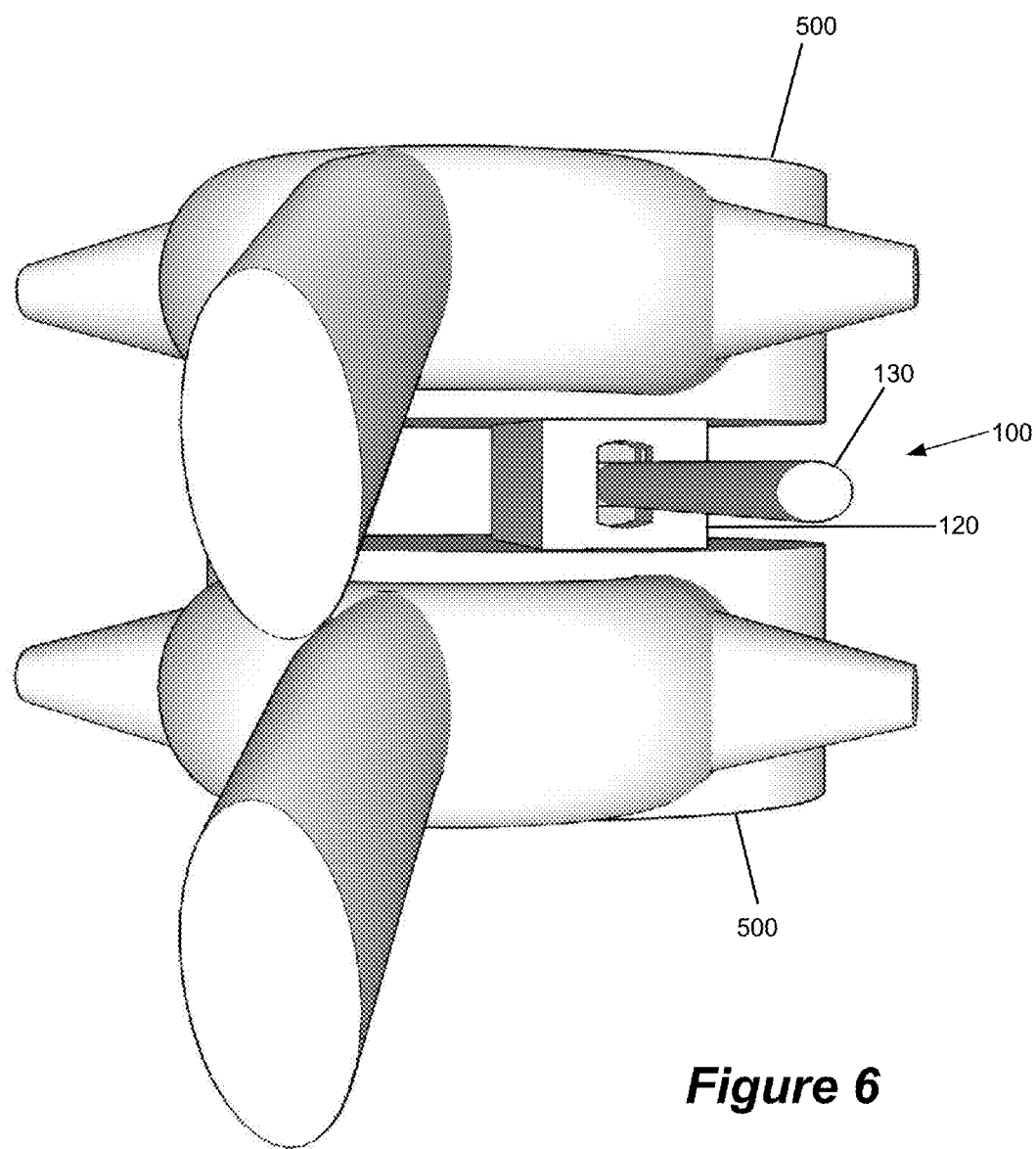
Figure 7:
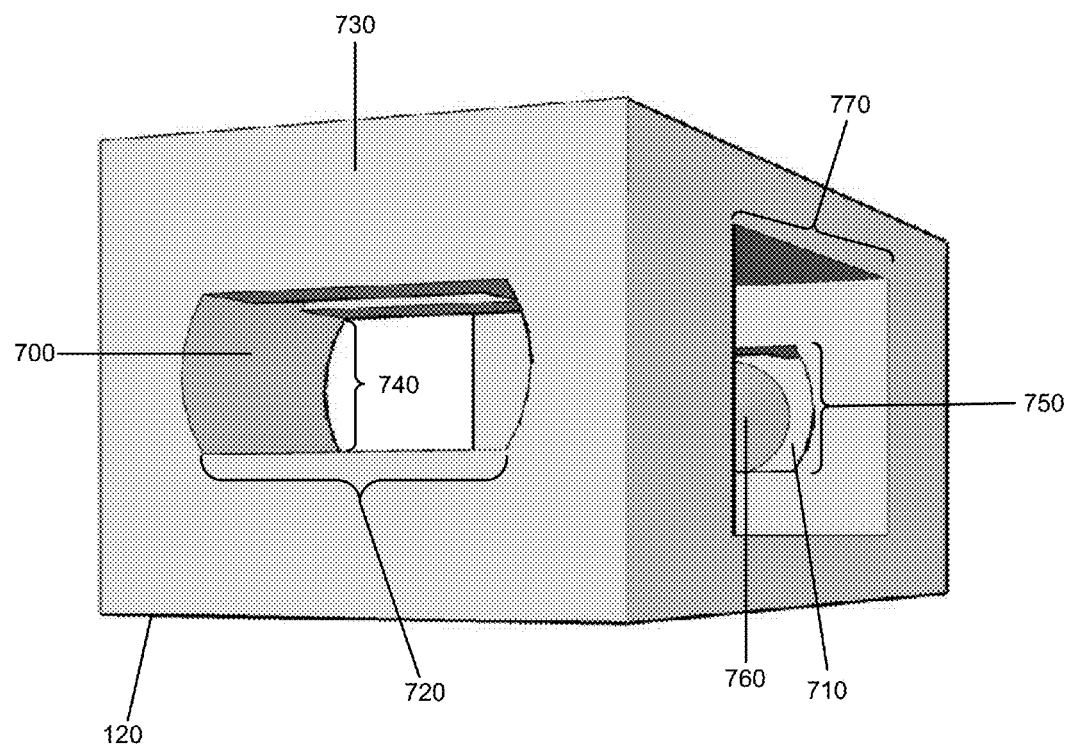
FIGS. 7-10 illustrate perspective views of the fusion member of some embodiments of the invention.
Figure 8:
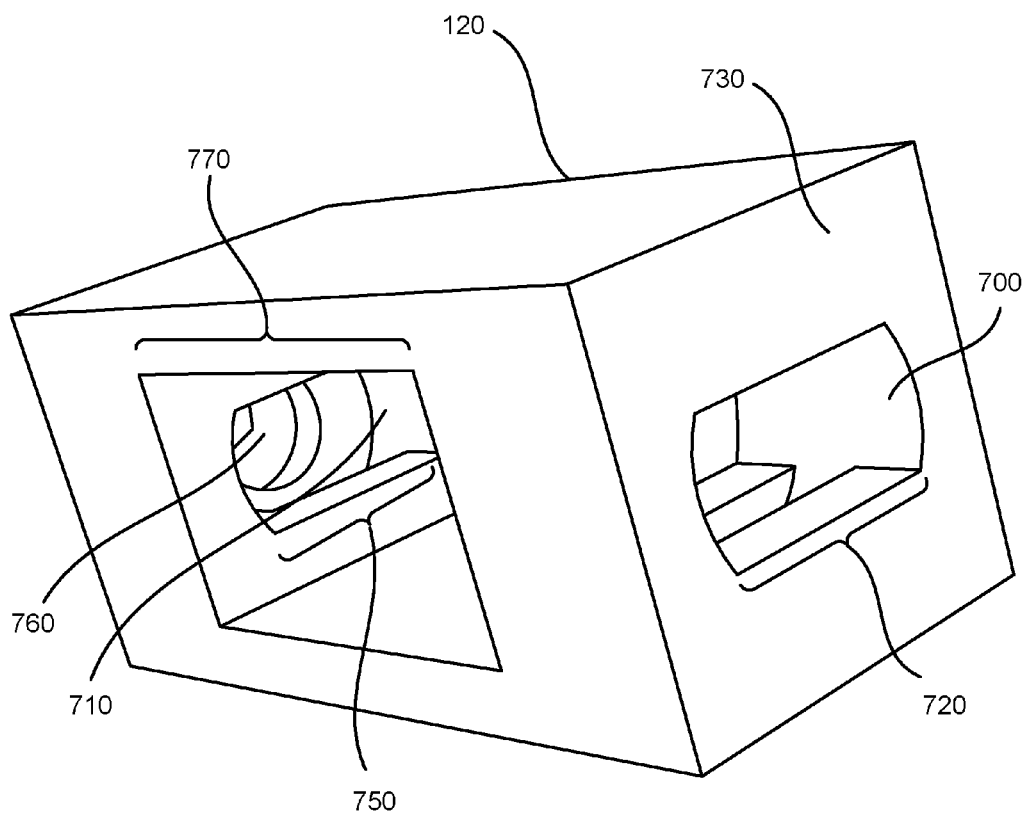
Figure 9:
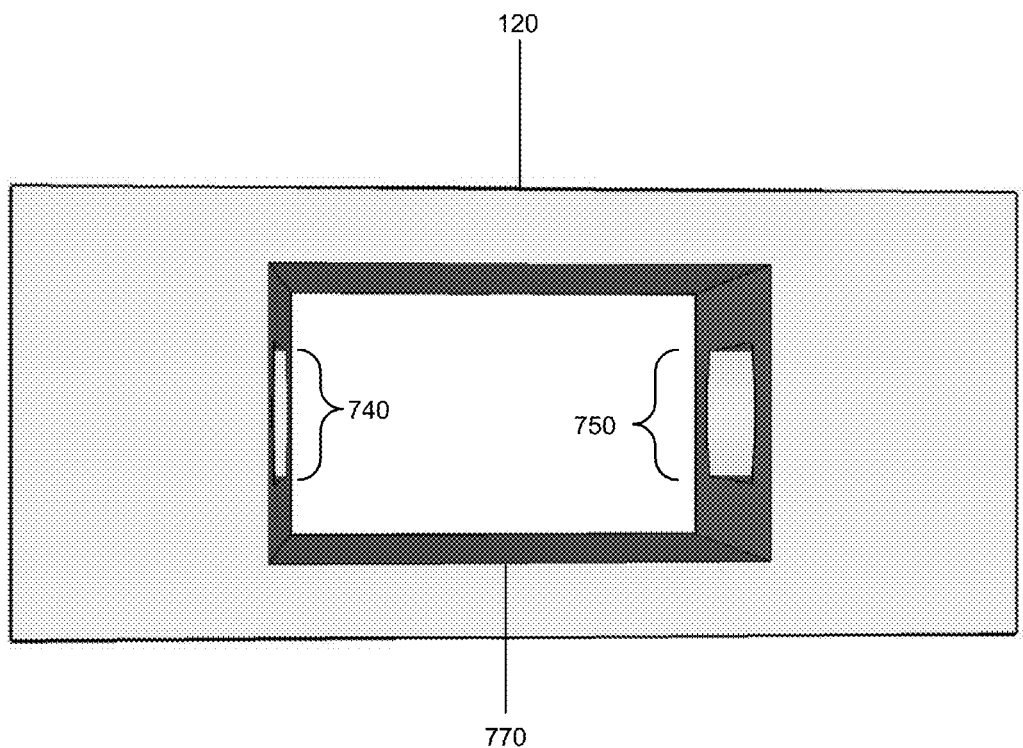

FIGS. 1-6 illustrate an example of one such apparatus according to some embodiments. FIGS. 1-4 provide different perspectives of an exploded view of the apparatus 100. FIG. 5 provides a side view of the assembled apparatus 100 in relation to two vertebral bodies 500 between which a fusion member 120 is placed. FIG. 6 provides a rear view of the assembled apparatus 100 in relation to the two vertebral bodies 500 between which the fusion member 120 is placed.

As shown in these figures, the apparatus 100 includes (1) a fusion member 120 that is delivered and positioned between the vertebral bodies 500 (2) a delivery member 130 that delivers and positions the fusion member 120 between the vertebral bodies 500 and (3) bone grafts 140-150 that can be placed inside the fusion member 120. Each of these components will be described in further detail below.

A. Fusion Member

As mentioned above, the apparatus 100 includes a fusion member 120 that is delivered and positioned between the vertebral bodies 500.

Figure 10:
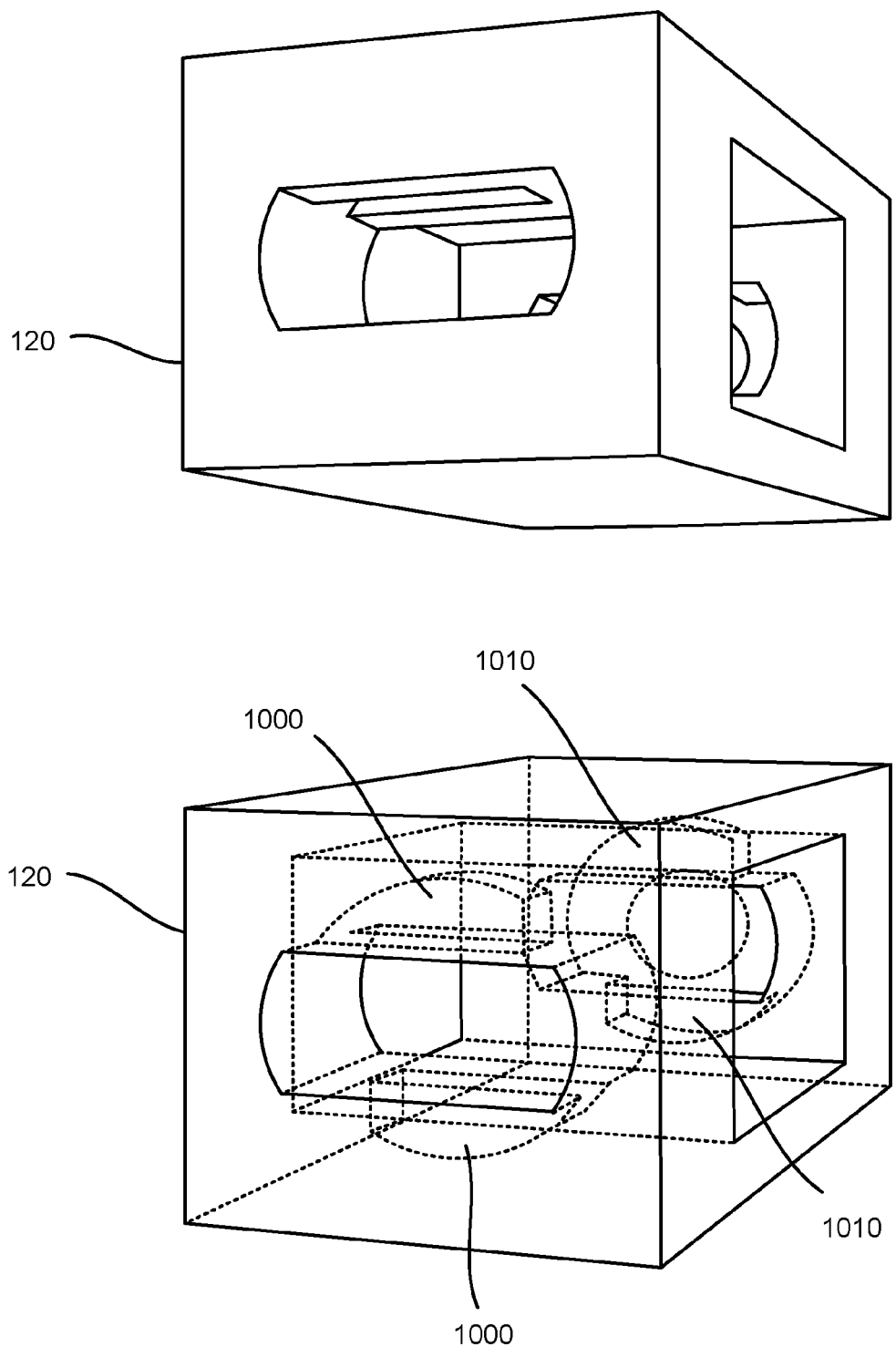

FIGS. 7-10 illustrate perspective views of the fusion member 120 of some embodiments of the invention. The fusion member 120 includes (1) two channels 700-710 through which the delivery member 130 can be advanced, (2) retention grooves (also called indentations) 1000-1010 of a retention mechanism for attaching the fusion member 120 to the delivery member 130, and (3) a cavity 770 for housing a first bone graft 140. In FIG. 10 and some of the subsequent figures, the fusion member 120 is shown transparently to facilitate an appreciation of the spatial relationships between the channels 700-710, channel openings 720, 740, and 750, the well 760, the retention grooves 1000-1010, and the cavity 770.

As shown in FIGS. 7-10, the fusion member 120 includes two channels 700 and 710 through which the delivery member can be inserted and advanced. A first channel 700 has an opening 720 on a proximal side 730 (i.e., side facing the medical practitioner) of the fusion member 120 and an opening 740 on the interior side of the fusion member 120. A second channel 710 has an opening 750 on the interior side of the fusion member 120 and a well 760 on a distal side (i.e., side opposite to the medical practitioner) of the fusion member 120. As shown in this figure, each channel 700-710 and its openings are rectangular in shape with two sides rounded to match the retention teeth of the delivery member. This shape allows the delivery member 130 to pass through the fusion member channels 700-710 and channel openings 720, 740, and 750 during insertion of the delivery member 130 into the fusion member 120 or during removal of the delivery member 130 from the fusion member 120. Typically, this shape has a length that ranges between 7 and 28 millimeters and a width that ranges between 4 and 16 millimeters. For the rounded sides of this shape, the shape has a diameter that ranges between 8 and 32 millimeters. The length and the diameter do not have to fall in these specified ranges in some embodiments.

Similarly, the well 760 on the distal side of the fusion member has an inverted cone shape to match a cone-shaped protrusion of the delivery member 130. This prevents the delivery member 130 from moving laterally while the delivery member 130 is inside the fusion member 120. The cone-shaped protrusion has a base with a diameter that ranges between 4 and 16 millimeters in some embodiments but the diameter does not have to fall in this range. One of ordinary skill in the art will recognize that the well 760 may have different shapes (e.g., an inverted dome shape or an inverted cylinder shape) as long as the shape of the well 760 and the protrusion of the delivery member 130 match and prevents the delivery member 130 from moving laterally while the delivery member 130 is inside the fusion member 120. The delivery member will be described in further detail below in Section B.

In some embodiments, the fusion member 120 does not have the well 760 on the distal side of the fusion member. Instead, the fusion member 120 of these embodiments has an opening on the distal side such that the second bone graft may be exposed through the opening when it is placed in a continuous channel that will be formed by the first and second channels and a channel within the first bone graft. This continuous channel will be described further below.

Figure 11:
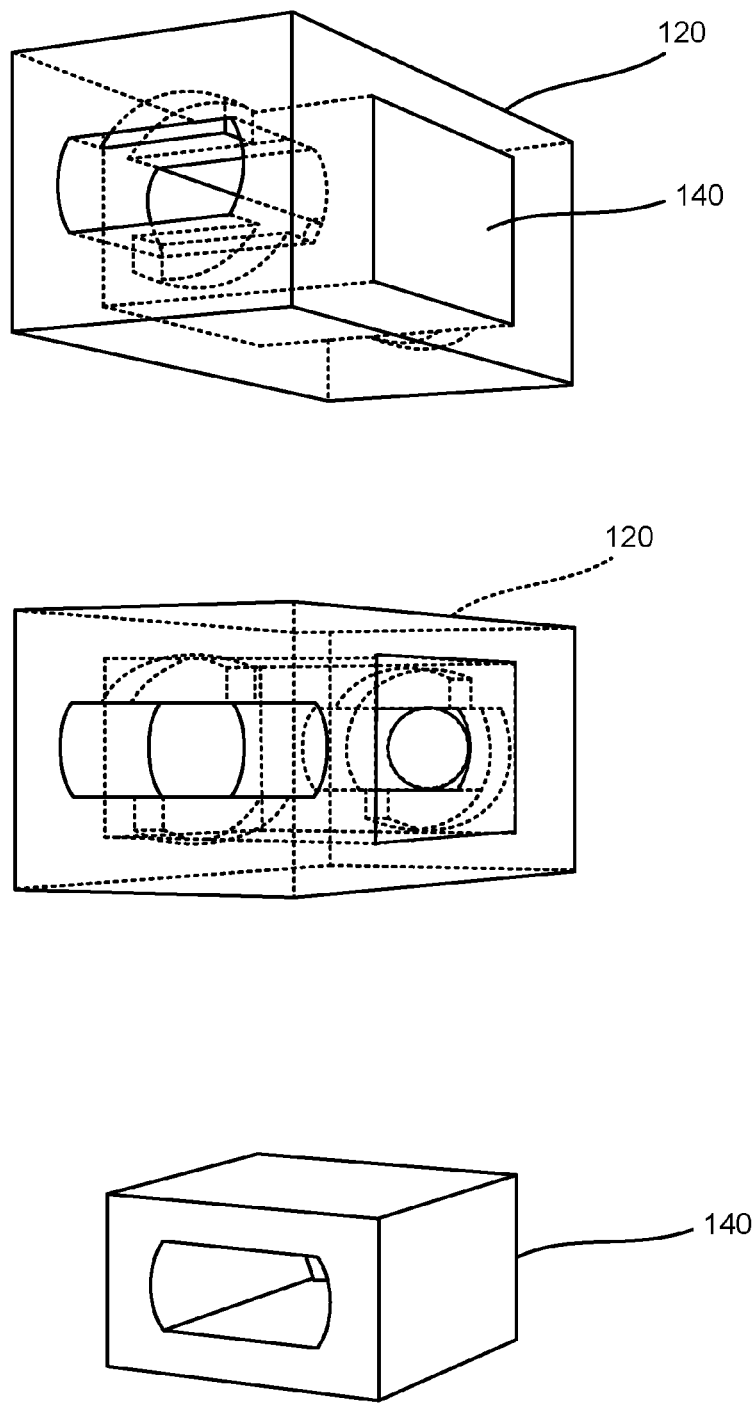
FIGS. 11-13 provide different perspectives of the fusion member with the bone graft inserted into the fusion member and without the bone graft inserted into the fusion member.
Figure 12:
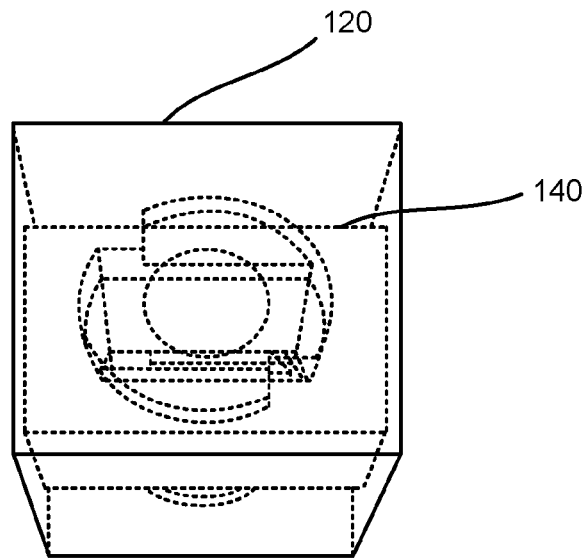
Figure 12:
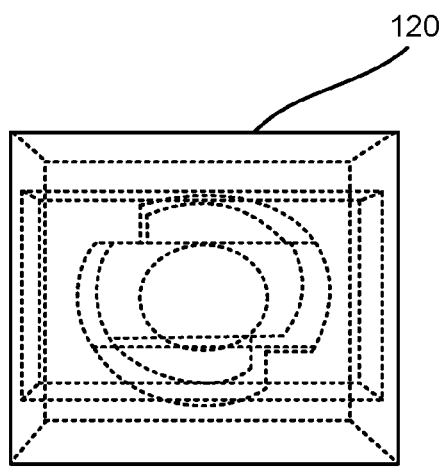
Figure 12:
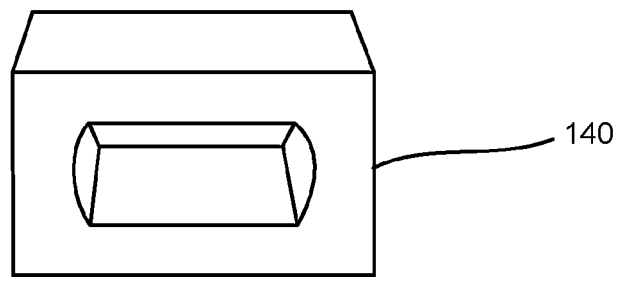
Figure 13:
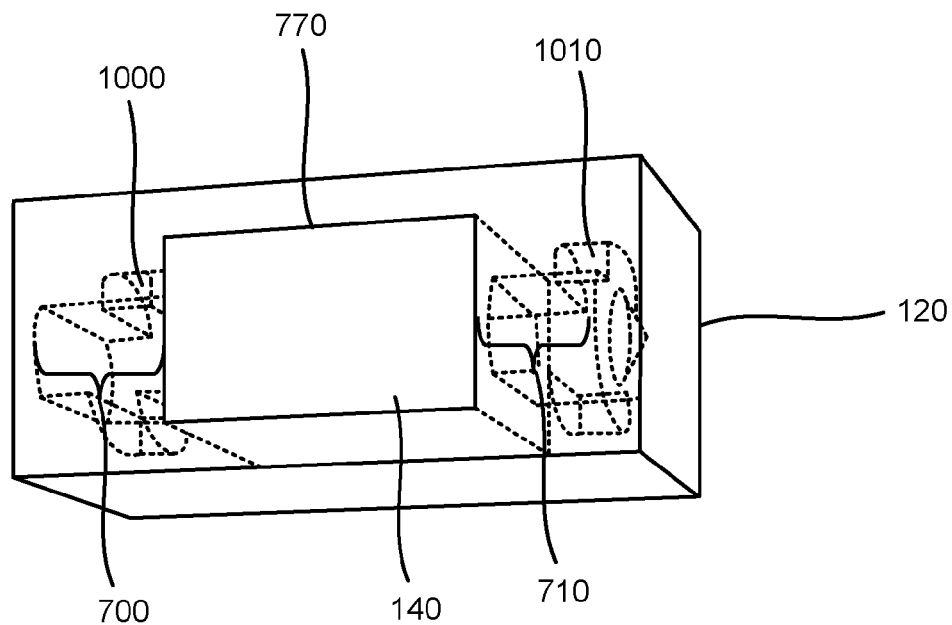
Figure 13:
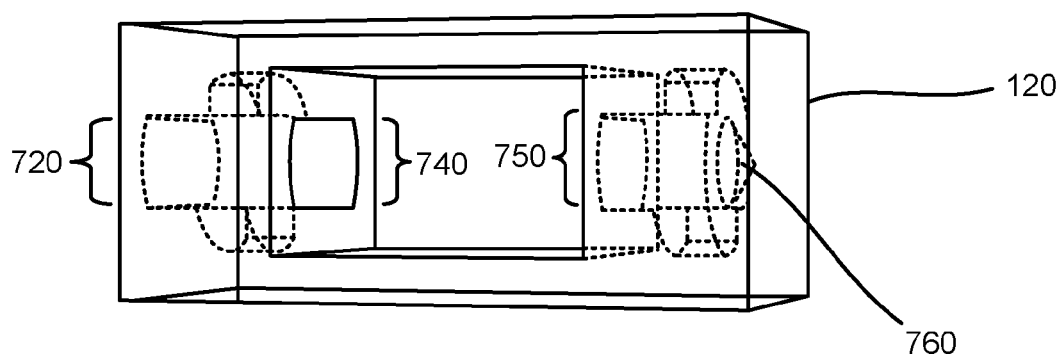
Figure 13:
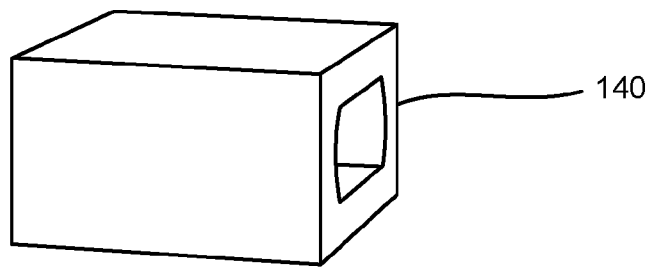

In addition, the fusion member 120 includes a cavity 770 in which the first bone graft 140 can be placed. The cavity 770 houses the first bone graft 140 once it has been inserted. One example of one such cavity is shown in FIGS. 11-13. FIGS. 11-13 provide different perspectives of the fusion member 120 with the first bone graft 140 placed in the fusion member 120 and without the first bone graft 140 placed in the fusion member 120. As shown in these figures, the cavity 770 is located in the center of the fusion member 120 between the two fusion member channels 700 and 710. In some embodiments, the first channel 700, the cavity 770, and the second channel 710 together extend from the proximal side 730 of the fusion member 120 to the distal side of the fusion member 120 and run the entire length of the fusion member 120. Typically, each of the first and second channels has a length that ranges between 6 and 24 millimeters. The entire length of the fusion member 120 ranges between 24 and 96 millimeters. The lengths of the channels and the fusion member 120 do not have to fall in their respectively specified ranges.

The first bone graft 140 can be placed in the cavity 770 in some embodiments. The first bone graft 140 includes a channel and channel openings that match the fusion member's channel 700 and 710 and channel openings 720, 740, and 750 to form a continuous channel that runs the entire length of the fusion member 120. In some embodiments, the channel of the first bone graft 140 may have a retention groove that can receive and engage a retention tooth of the fusion member 120.

In some embodiments, a second bone graft 150 can be placed in the continuous channel after the delivery member 130 is removed from the fusion member 120. In addition, the first channel 700, the cavity 770, and the second channel 710 are parallel to the top, bottom, left, and right sides of the fusion member 120, but perpendicular to the proximal and distal sides of the fusion member 120. This allows the channel openings 720, 740, and 750 to be located on the center of each face of the fusion member 120.

In some embodiments, the fusion member 120 does not have the cavity 770. Instead, the fusion member 120 of these embodiments has a continuous channel that runs the entire length of the fusion member 120. This continuous channel has one or more grooves to receive and engage one or more retention teeth of the delivery member 130.

In some embodiments, two retention grooves 1000 and 1010 couple the fusion member 120 with the delivery member 130. The two retention grooves 1000 and 1010 are shown in FIGS. 11-13. The first retention groove 1000 is located between the opening 720 on the proximal side 730 of the fusion member 120 and the interior opening 740 of channel 700. The second retention groove 1010 is located between the interior opening 750 of the second channel 710 and the well 760 on the distal side of the fusion member 120.

Figure 14:
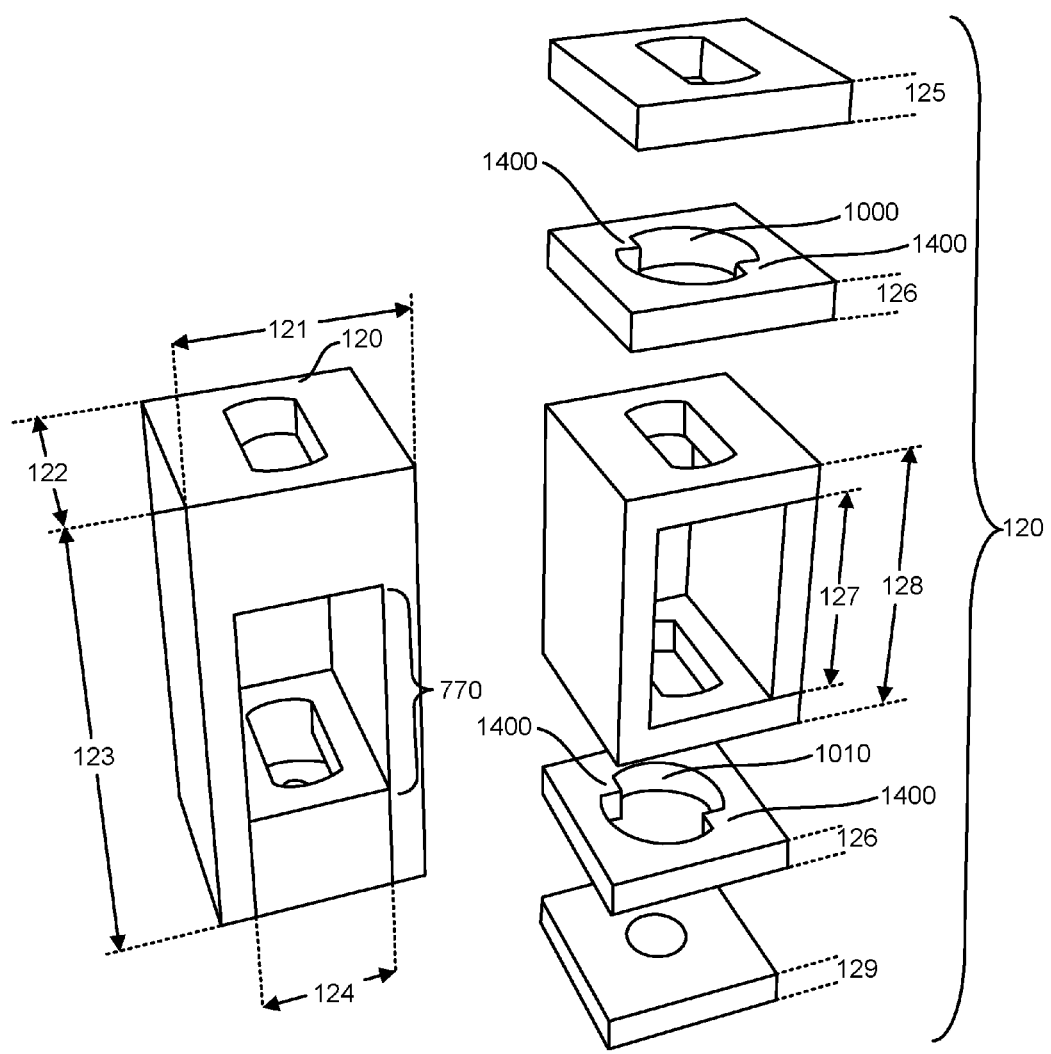
FIG. 14 illustrates the fusion member in multiple cross-sections to provide a clear view of the retention grooves.

FIG. 14 illustrates the fusion member 120 in multiple cross-sections to provide a clear view of the retention grooves 1000-1010. Each retention grove 1000-1010 is circular in shape with two protruding tips 1400. The circular shape of each retention groove 1000-1010 allows the retention teeth of the delivery member 130 to be rotated once the delivery member 130 has been inserted and fully advanced into the fusion member 120. The diameter of the retention groove 1000-1010 is about the same as the length of the channel openings 720, 740, and 750 and the delivery member's retention teeth. This allows the retention teeth of the delivery member to pass through each channel 700-710 and channel openings 720, 740, and 750. Typically, the diameter of the retention groove 1000-1010 ranges between 8 and 32 millimeters. The width 126 of each retention groove 1000-1010 (i.e., the length of the groove along the length of the fusion member channels 700-710) ranges between 2 and 8 millimeters. The width of the retention groove is about the same as the depth of the delivery member's retention teeth (i.e., the length of the teeth along the length of the longitudinal axis of the delivery member 130). The diameter and widths 126 do not have to fall in their respectively specified ranges.

The diameter of each retention groove 1000-1010 is greater than the width of each channel 700-710 and channel openings 720, 740, and 750. This prevents any lateral and longitudinal movement of the delivery member 130 when the delivery member 130 and delivery member's retention teeth are at an angle (e.g., 90 degrees) compared in relation with the fusion member channels 700-710 and channel openings 720, 740, and 750 since the length of the delivery member's retention teeth is greater that the width of each channel opening 720, 740, and 750. The width of each channel opening 720, 740, and 750 ranges between 4 and 16 millimeters but the width does not have to fall in this range. The protruding tips 1400 prevent the delivery member from being rotated more than a certain number of degrees (e.g., 90 degrees), allowing the delivery member's retention teeth to either (1) align to with each channel opening 720, 740, and 750 or (2) be angled with (e.g., be perpendicular to) each channel opening 720, 740, and 750. The delivery member 130 will be described in further detail below.

In some embodiments, the diameter of each retention grove 1000-1010 and the length of each retention teeth may vary along the direction of the rotation of the retention teeth. This will allow the tooth and groove to unlock in only one direction of rotation. Also, the width of each retention groove (i.e., the length of the groove along the length of the fusion member channels 700-710) and the depth of the delivery member's retention teeth (i.e., the length of the teeth along the length of the longitudinal axis of the delivery member 130) may vary. For instance, the depth of the retention tooth may taper in the direction that points away from the longitudinal axis of the delivery member 130 or taper in the direction that points into the longitudinal axis of the delivery member 130 in some embodiments. The width of the groove in these embodiments tapers in both directions accordingly.

Height 121 specifies the height of the fusion member 120. Typically, the height 121 ranges between 12 and 48 millimeters, but it does not have to fall in this range. Width 122 specifies the width of the fusion member 120. The width 122 ranges between 12 and 48 millimeters, but it does not have to fall in this range. Length 123 specifies the length of the fusion member 120. Typically, the length 123 ranges between 24 and 96 millimeters, but it does not have to fall in this range. Height 124 specifies the height of the cavity 770. Typically, the height 124 ranges between 8 and 32 millimeters, but it does not have to fall in this range.

Length 125 specifies the length of a portion of the first channel 700 that is before the retention groove 1000. The length 125 typically ranges between 2 and 8 millimeters, but it does not have to fall in this range. Width 127 specifies the width of the cavity 770. The width 127 typically ranges between 12 and 48 millimeters, it does not have to fall in this range. Length 128 specifies the length between the end of retention groove 1000 and the beginning of the retention groove 1010. The length 128 typically ranges between 16 and 64 millimeters, but it does not have to fall in this range. Length 129 specifies the length of a portion the fusion member 120 between the distal side of the fusion member 120 and the end of retention groove 1010. The length 129 typically ranges between 2 to 8 millimeters, but it does not have to fall in this range.

In some embodiments, the retention grooves 1000-1010 of the fusion member 120 couple with delivery member 130 to form a retention mechanism. The retention teeth of the delivery member are the male coupling members of the retention mechanism while the retention grooves of the fusion members are the female coupling members of this mechanism.

One of ordinary skill in the art will realize that there can be any number of fusion member channels in the fusion member. The fusion member channels can be of various shapes and sizes to accommodate the various shapes and sizes of the delivery member.

One of ordinary skill in the art will realize that the retention mechanism and retention grooves can be in another location on the fusion member, such as on the exterior of the fusion member, and can vary in shape, size, and number. Also, other embodiments might have different retention mechanisms. For instance, in some embodiments, the retention teeth are on the fusion member while the retention grooves are on the delivery member. Moreover, instead of, or in conjunction with, this tooth and groove approach, one of ordinary skill will realize that other embodiments use other retention structures (e.g., other male/female structures, other structures such as expandable clasps that encapsulate the lateral edges of the fusion member, other structures such as a clamp, etc.) to affix the delivery member to the fusion member.

In some embodiments, the fusion member can be composed of any number of materials, such as metals (e.g., stainless steel, titanium, or nitinol), various polymers (e.g., PMMA or polyetheretherketone), carbon fiber, etc. The fusion member can also be partially or be completely made of bioabsorbable or biodegradable materials, so that it can be partially or be completely absorbed. In some embodiments, the fusion member's faces that are in contact with the vertebral endplates may have surface contours such as ridges to enhance stability. The fusion member can also include additional channels or cavities to be packed with bone graft material or bone graft substitutes to enhance progressive solid bony fusion. Bone graft material and bone graft substitutes can also be packed into the intervertebral space surrounding and between the fusion members to enhance progressive solid bony fusion. The fusion member can also be coated with or partially be composed of human bone morphogenetic protein or other bone growth inducing substances.

Typically, the fusion member is inserted between adjacent vertebral bodies after at least some of the fibrocartilaginous disc between the adjacent vertebral bodies is removed during a partial or complete discectomy. Once the fusion member is delivered to the proper location between adjacent vertebral bodies, two or more sides of the fusion member may be in contact with the opposed endplates of the adjacent vertebral bodies. These contacting sides in some embodiments restore both disc height and physiologic lordosis. In some embodiments, these sides are parallel to each other, whereas in other embodiments, these sides are nonparallel such that the fusion member presents a tapered profile when viewed laterally. The delivery member that inserts the fusion member between the vertebral bodies will be described below.

B. Retention Mechanism and Delivery Member

Figure 15:
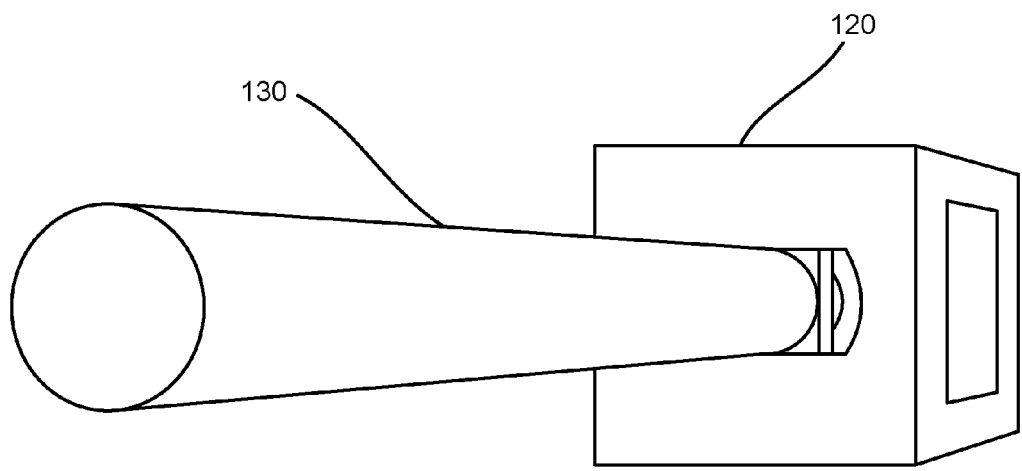
FIGS. 15-16 show different perspectives of the delivery member coupled with the fusion member.
Figure 16:
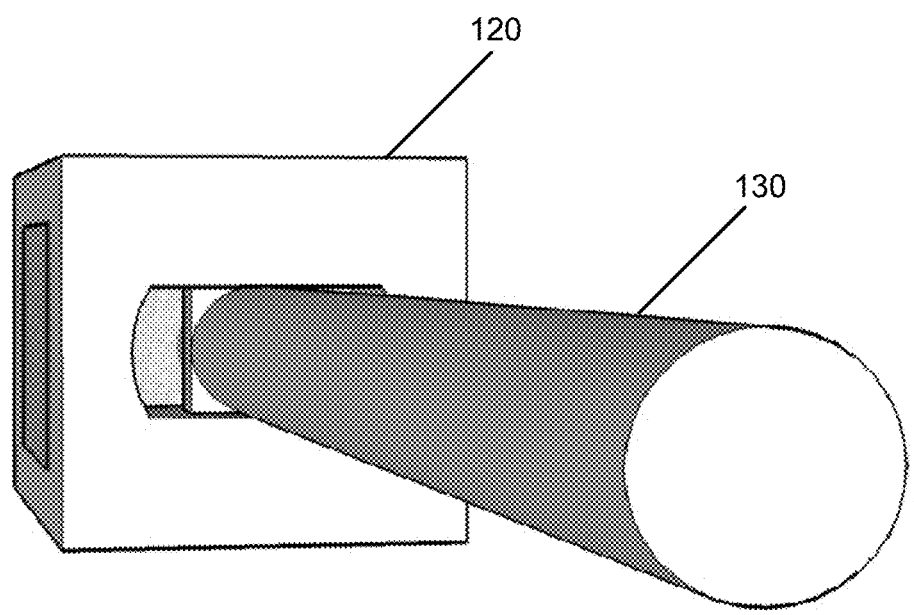

As mentioned above, the retention mechanism attaches the delivery member 130 to the fusion member 120. FIGS. 15-16 show different perspectives of the delivery member 130 coupled with the fusion member 120. In some embodiments, the retention mechanism is used as a way of controllably detaching the delivery member 130 from the fusion member 120 after the medical practitioner determines that the fusion member 120 is placed at the desired position between two vertebral bodies.

Figure 17A:
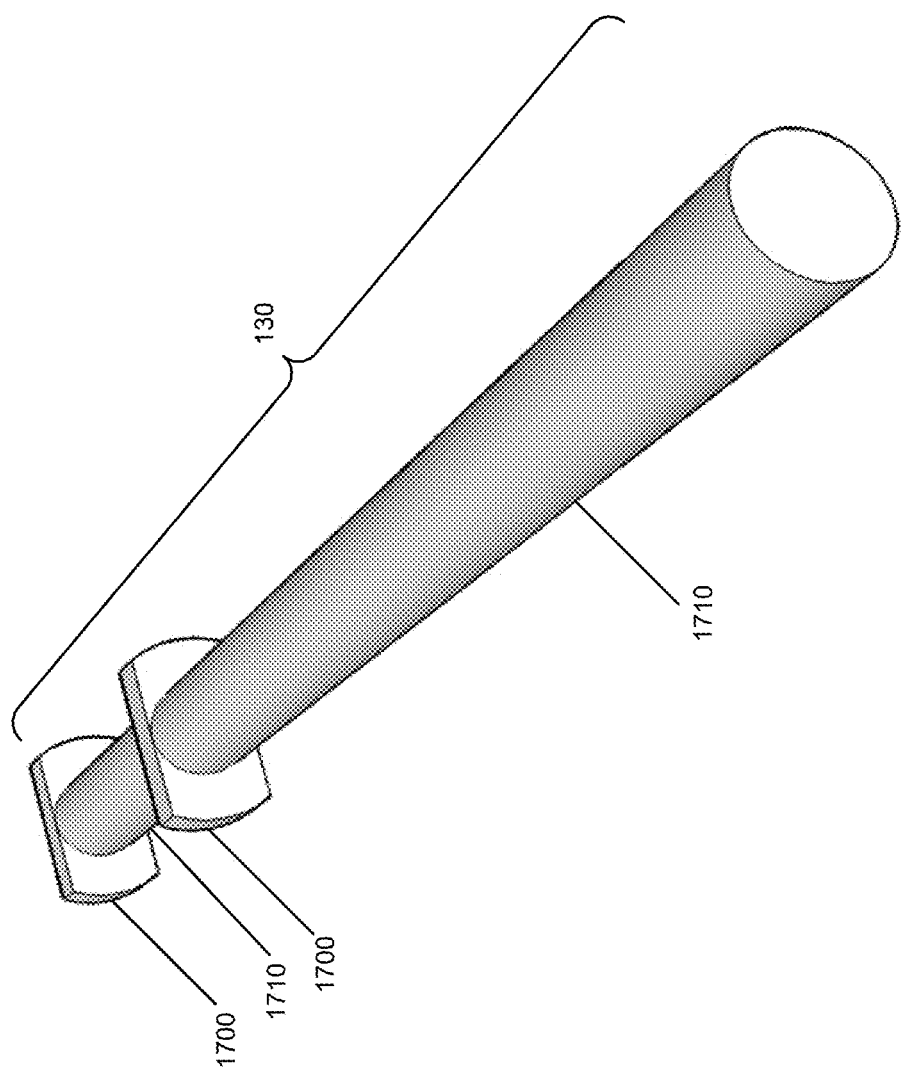
FIG. 17A-17C show detailed views of the delivery member from different perspectives.
Figure 17B:
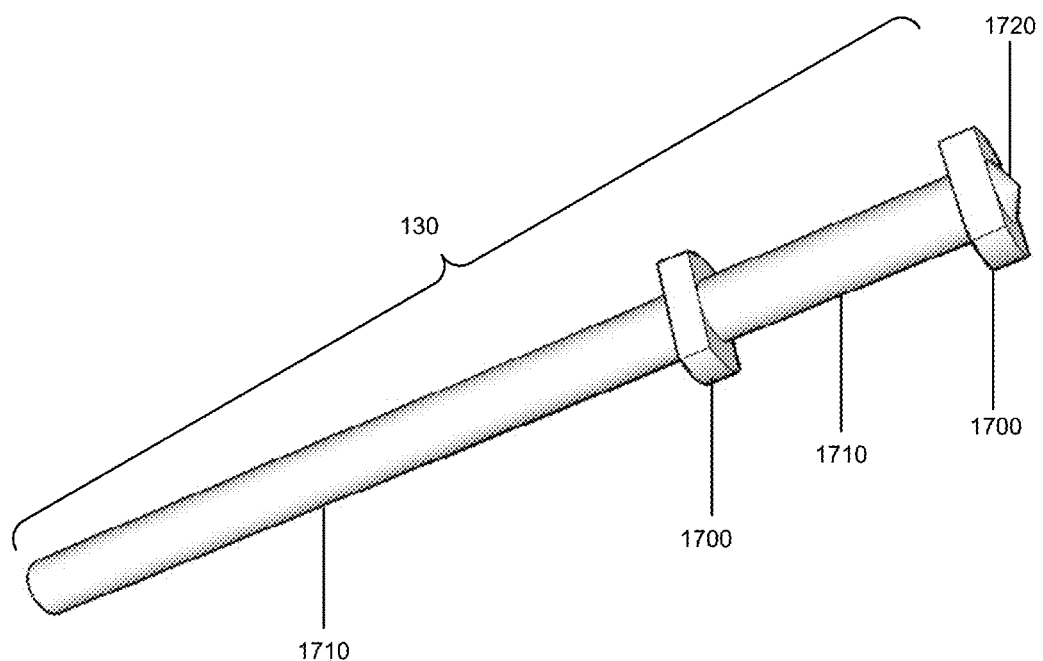
Figure 17C:
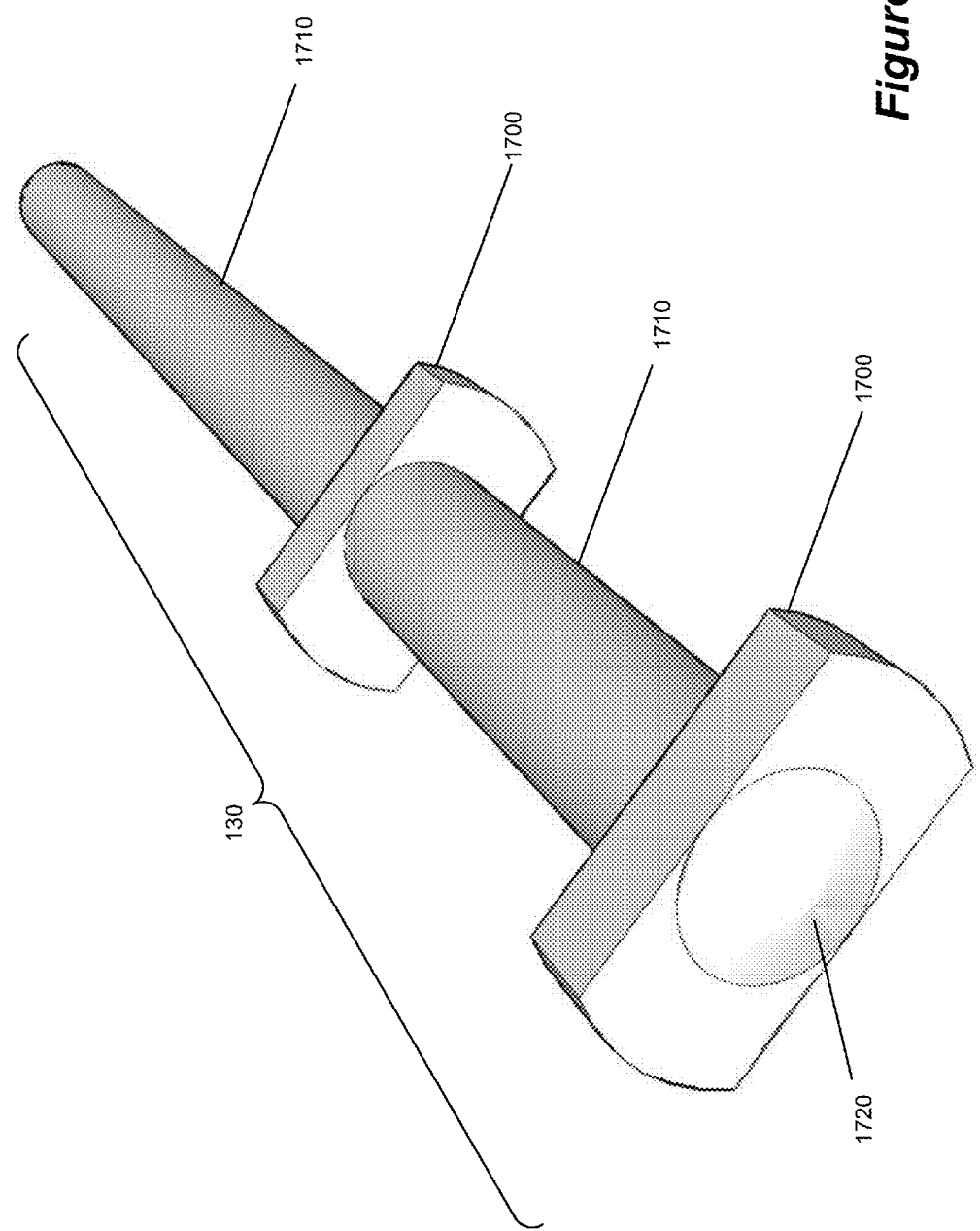

The retention mechanism that is illustrated in FIGS. 15-16 includes (1) a delivery member 130, and (2) a set of retention grooves 1000-1010 (not transparently shown) of the fusion member 120, which couple with delivery member 130. FIGS. 17A-17C show detailed views of the delivery member from different perspectives. As shown in FIGS. 17A-17C, each delivery member 130 in some embodiments includes (1) a rod 1710 with a distal end from which retention teeth 1700 protrude, (2) retention teeth 1700 on the distal end of the rod 1710 that couple with the retention grooves 1000-1010, and (3) a protrusion 1720 on the distal end of the rod 1710. In some embodiments, there is a handle on the proximal end of the rod 1710 (not pictured) that rotates the delivery member 130 about the longitudinal axis of the rod. Typically, the length of the rod ranges between 70 and 300 millimeters but the length does not have to fall in this range.

Figure 18:
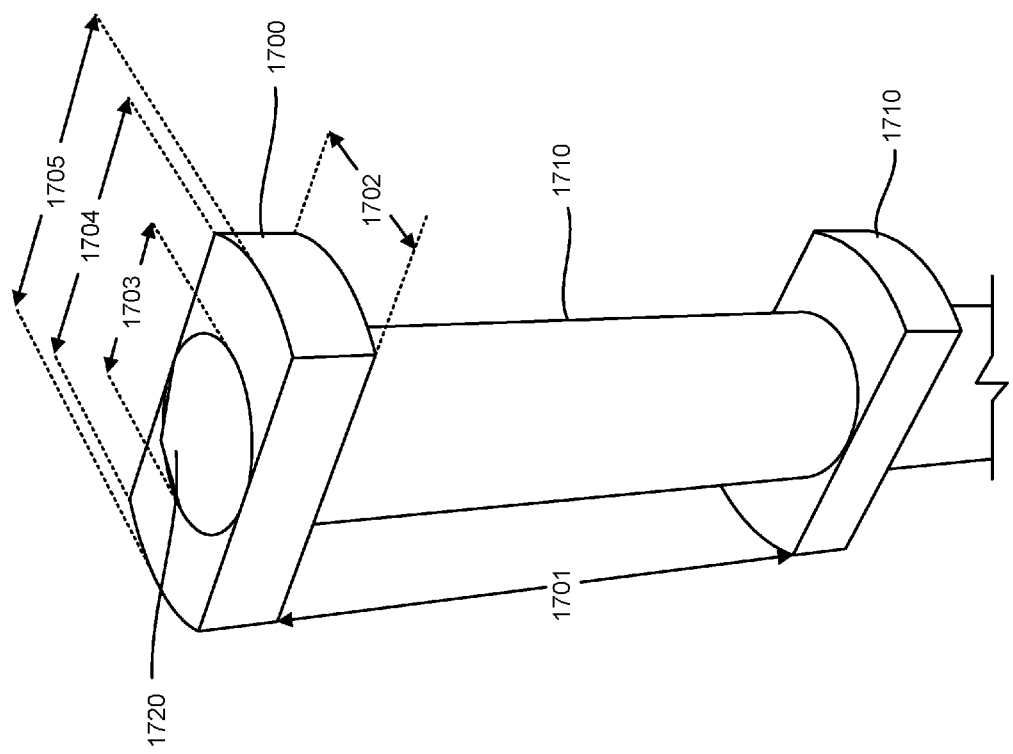
FIG. 18 shows a close-up view of two retention teeth of the delivery member.

FIG. 18 shows a close-up view of two retention teeth 1700 of the delivery member 130 and the protrusion 1720. As described above, the retention teeth 1700 are in the same shape as the fusion member channels 700-710 and channel openings 720, 740, and 750, which allow the delivery member 130 to pass through the fusion member channels 700-710 in some embodiments. As shown, each the retention teeth 1700 protrudes from the rod 1710 in two directions that are opposite to each other in some embodiments to form a rectangular shape with two sides that are rounded. These two rounded sides, in turn, form part of a circle to facilitate the rotation along the retention grooves of the fusion member.

As described above, the diameter of each retention grove 1000-1010 and the length of each retention teeth 1700 (i.e., the length between a point on the side of the rectangular shape and the longitudinal axis of the rod 1710) may vary along the direction of the rotation of the retention teeth 1700. This will allow the tooth and groove to unlock in only one direction of rotation. Also, the width of each retention groove (i.e., the length of the groove along the length of the fusion member channels 700-710) and the depth of the delivery member's retention teeth (i.e., the length of the teeth along the length of the longitudinal axis of the delivery member 130) may vary. For instance, the depth of the retention tooth may taper in the direction that points away from the longitudinal axis of the delivery member 130 or taper in the direction that points into the longitudinal axis of the delivery member 130 in some embodiments. The width of the groove in these embodiments tapers in both directions accordingly.

Some embodiments may have different shapes for the retention teeth 1700 and the fusion member channels 700-710 as long as the delivery member 130 can pass through the fusion member channels 700-710 and rotate to engage the fusion member 120. For instance, instead of having each tooth protruding in two directions that are opposite to each other, some embodiments may have each tooth protruding in more than two directions from the rod 1710. Some embodiments may also have each tooth protruding in different directions from the rod 1710.

As described above, the protrusion 1720 has a shape that matches with the shape of the well 760 of the fusion member 120. In some embodiments, the protrusion 1720 is shaped like a cone. In these embodiments, the cone has a base of which the diameter ranges between 4 and 16 millimeters but the diameter does not have to fall in this range. One of ordinary skill in the art will recognize that the protrusion 1720 may have different shapes (e.g., a dome shape or a cylinder) as long as the shape of the protrusion 1720 and the well 760 of the fusion member 120 match and prevents the delivery member 130 from moving laterally while the delivery member 130 is inside the fusion member 120.

Length 1701 specifies the length of a portion of the rod that is between the two retention teeth 1700. The length 1701 typically ranges from 16 and 64 millimeters, but it does not have to fall in this range. Width 1702 specifies the width of each retention tooth 1700. The width typically ranges between 4 and 16 millimeters, but it does not have to fall in this range. Diameter 1703 specifies the diameter of the base of the protrusion 1720. The diameter 1703 typically ranges between 4 to 16 millimeters, but it does not have to fall in this range. Length 1704 specifies the length of a straight side of each retention tooth 1700. The length 1704 typically ranges between 7 to 28 millimeters, but it does not have to fall in this range. Diameter 1705 defines the diameter of a circle of which the circular sides of each retention tooth 1700 make up a portion. The diameter 1705 typically ranges between 8 to 32 millimeters, but it does not have to fall in this range.

Figure 19:
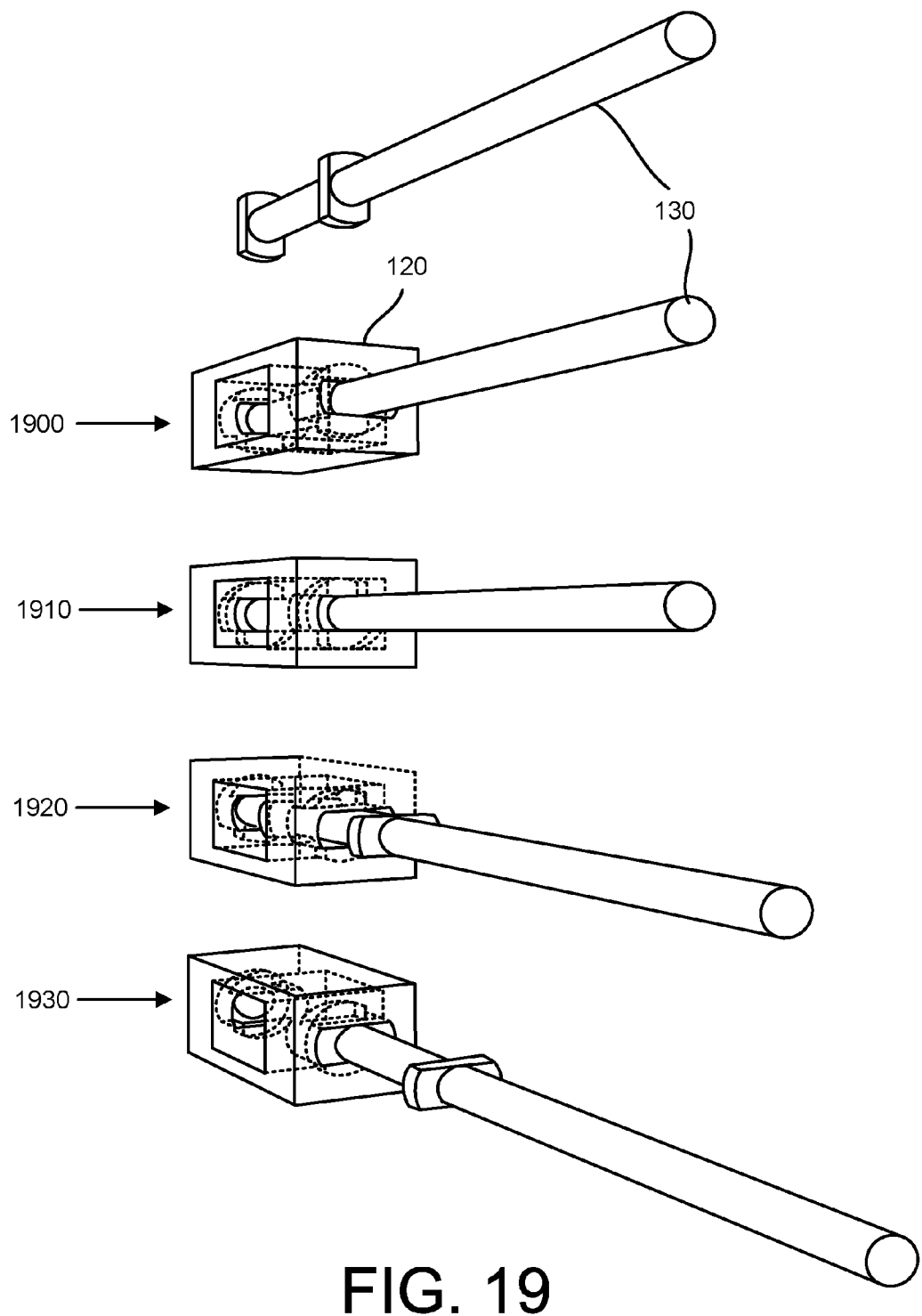
FIGS. 19-20 step through an example of the process of controllably detaching the delivery member from the fusion member once the medical practitioner determines that the fusion member is in the proper location between the vertebral bodies between which the fusion member is placed.
Figure 20:
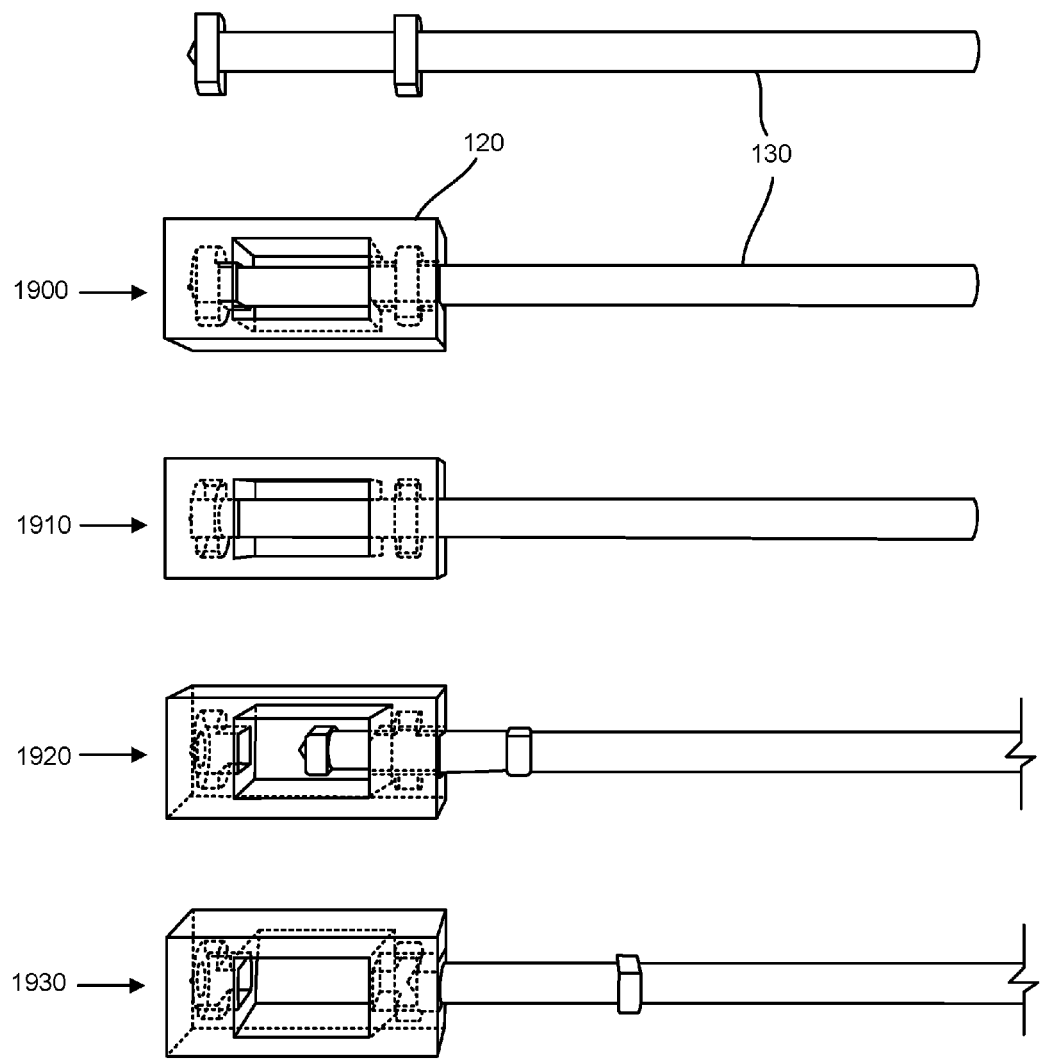

FIGS. 19-20 step through an example of the process of controllably detaching the delivery member 130 from the fusion member 120 once the medical practitioner determines that the fusion member 120 is in the proper location between the vertebral bodies between which the fusion member 120 is placed. Each of these figures shows the initial configuration 1900 of delivery member 130 fully coupled with the fusion member 120. In this configuration, the two retention grooves 1000-1010 of the fusion member 120 are fully coupled with the retention teeth 1700 of the delivery member 130. The retention teeth 1700 in this configuration are angled with (e.g., are perpendicular to) the channel openings 720, 740, and 750 of the fusion member channels 700-710, which prevents any lateral, vertical, or horizontal movement of the delivery member 130 in relation to the fusion member 120. In other words, the delivery member 130 is locked to the fusion member 120 in this configuration. This configuration allows the fusion member 120 to be delivered between adjacent vertebral bodies. The top of each figure shows the delivery member 130 in the initial configuration 1900 without the fusion member 120.

After the fusion member 120 has been delivered, a medical practitioner determines (e.g., by viewing x-ray images of the patient) whether the fusion member 120 is in the correct position. If a determination is made that fusion member 120 is not in the correct position between two vertebral bodies, the delivery member 130 can be used to reposition the fusion member 120 to the desired location. When the medical practitioner determines that the fusion member 120 is placed at the desired position between two vertebral bodies, the retention mechanism can be used to controllably detach the delivery member 130 from the fusion member 120. The controllable detachment of the delivery member 130 from the fusion member 120 is initiated by the uncoupling of the delivery member's retention teeth 1700 from each retention groove 1000-1010 of the fusion member 120.

Configuration 1910 shows the delivery member 130 partially uncoupled from the retention grooves 1000-1010 of the fusion member 120. In this configuration, the delivery member 130 is rotated a certain number of degrees (e.g., 90 degrees) from the position in configuration 1900 so that the retention teeth 1700 are aligned with channel openings 720, 740, and 750 of each fusion member channel 700-710. This configuration disengages the retention teeth 1700 from the retention grooves 1000-1010, aligns the retention teeth 1700 with the channel openings 720, 740, and 750 of each fusion member channel 700-710, and allows the delivery member 130 to be withdrawn from the fusion member 120.

Configuration 1920 shows the distal end of the delivery member 130 after the delivery member 130 has been pulled away from the fusion member 120 so that it is no longer in contact with the retention grooves 1000-1010 (i.e., it has been removed from the retention groove). Once the delivery member 130 has been withdrawn from the retention grooves 1000-1010 and from the fusion member 120 as shown in configuration 1930, it can be removed from the patient.

One of ordinary skill in the art will realize that alternative structures can be used for the retention groove and teeth structures than those illustrated in FIGS. 19-20. Moreover, one of ordinary skill in the art will also realize that different configurations and different numbers of retention teeth can be utilized to affix the delivery member to the fusion member. In some embodiments, the retention teeth may be on the fusion member and the retention groove may be on the delivery member. Instead of, or in conjunction with, this tooth and groove approach, other embodiments of the invention can use other structures (e.g., other male/female structures, other structures such as expandable clasps that encapsulate the lateral edges of the fusion member, other structures such as a clamp, etc.) to affix the delivery member to the fusion member.

As mentioned above, the delivery member can be passed through the fusion member channels. Different embodiments have different channels for allowing the delivery member to pass through. In some embodiments, a circular channel with a constant diameter throughout its entire length allows the delivery member to pass through. Other embodiments have channels of different shapes and sizes. One such alternative embodiment (now shown) is a square or rectangular channel with increasing and decreasing diameter towards the distal side of the fusion member.

C. Fusion Apparatus

In some embodiments, the intervertebral fusion apparatus that includes the fusion member and delivery member is already pre-assembled. However, in different embodiments, the fusion apparatus may be pre-assembled to different degrees. For instance, in some embodiments, the first bone graft may already be inserted into the fusion member while the delivery member is not. In other embodiments, the first bone graft and the delivery member may be fully assembled with the fusion member. In some embodiments, the first bone graft may be fully assembled with the fusion member, but the delivery member may only be partially inserted into the fusion member channel. Yet, in other embodiments, the delivery member is not inserted at all in the fusion member channel and may be inserted into the apparatus when needed.

III. Example of a Fusion Procedure

Figure 21:
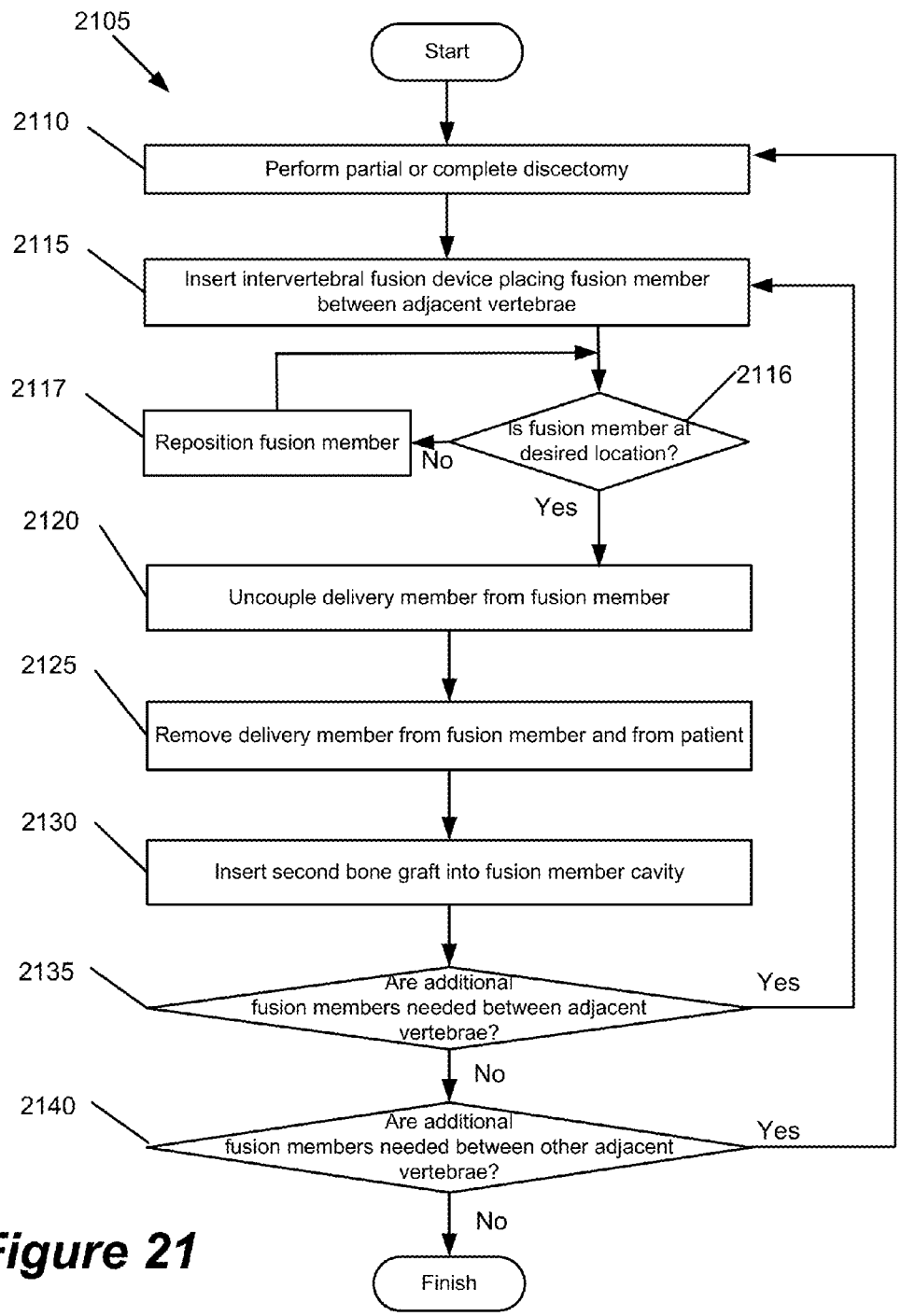
FIG. 21 depicts a medical procedure that involves the insertion of the apparatus of some embodiments of the invention.

The operation of the apparatus 100 will now be described. FIG. 21 depicts a medical procedure 2105 that involves the insertion of the apparatus 100 of some embodiments of the invention. In this procedure, a medical practitioner (e.g., a physician or a machine) initially performs (at 2110) a partial or complete discectomy, which typically involves making an incision in a patient and removing some or all of the fibrocartilaginous disc between two adjacent vertebral bodies. Any number of known techniques/procedures can be used to remove the disc at 2110.

Next, the medical practitioner inserts the intervertebral fusion device (at 2115) and positions (at 2115) the fusion member (e.g., one of the blocks described above) between the endplates of adjacent vertebrae. Any number of known techniques/procedures for inserting a fusion member between two adjacent vertebrae can be used (at 2115) to insert the intervertebral fusion device and position the interbody fusion member between adjacent vertebrae. One technique for inserting the fusion member involves the use of the delivery member (e.g., apparatus 130 described above).

Next, the medical practitioner determines (at 2116) whether the fusion member is placed at a desired location between two vertebral bodies. In some embodiments, a radiograph or x-ray of the patient may be taken to determine if the fusion member is placed at an appropriate position between two vertebral bodies.

When the medical practitioner determines (at 2116) that the fusion member is not placed at a desired position between two vertebral bodies, the medical practitioner attempts to reposition (at 2117) the fusion member to the desired location. The medical practitioner then loops back to 2116 to determine whether the fusion member is placed at the desired location.

When the medical practitioner determines (at 2116) that the fusion member is placed at a desired position between two vertebral bodies, the medical practitioner uncouples (at 2120) the delivery member from the fusion member. In some embodiments, this is achieved by rotating the delivery member a certain number of degrees (e.g., 90 degrees) so that the retention teeth of the delivery member disengage from the retention grooves of the fusion member. Once uncoupled, the delivery member may be separated from the fusion member, and the delivery member may then be removed (at 2125) from the patient. In some embodiments, robotic arms may be used to uncouple the delivery member from the fusion member and remove the delivery member from the fusion member and from the patient.

Once the delivery member has been removed from the fusion member, the medical practitioner inserts (at 2130) a second bone graft into the cavity of the fusion member. In some embodiments, more than one fusion member is inserted between two adjacent vertebral bodies. Accordingly, the medical practitioner determines (at 2135) whether another fusion member needs to be inserted between the vertebral bodies between which the last fusion member was inserted (at 2115). If so, the medical procedure is repeated from 2115 to 2130. Also, in some embodiments, the medical procedure 2105 is performed multiple times to replace multiple discs between multiple pairs of vertebral bodies.

IV. Fusion Members with Ridges and Additional Bone-Grafting Cavities

Figure 22:
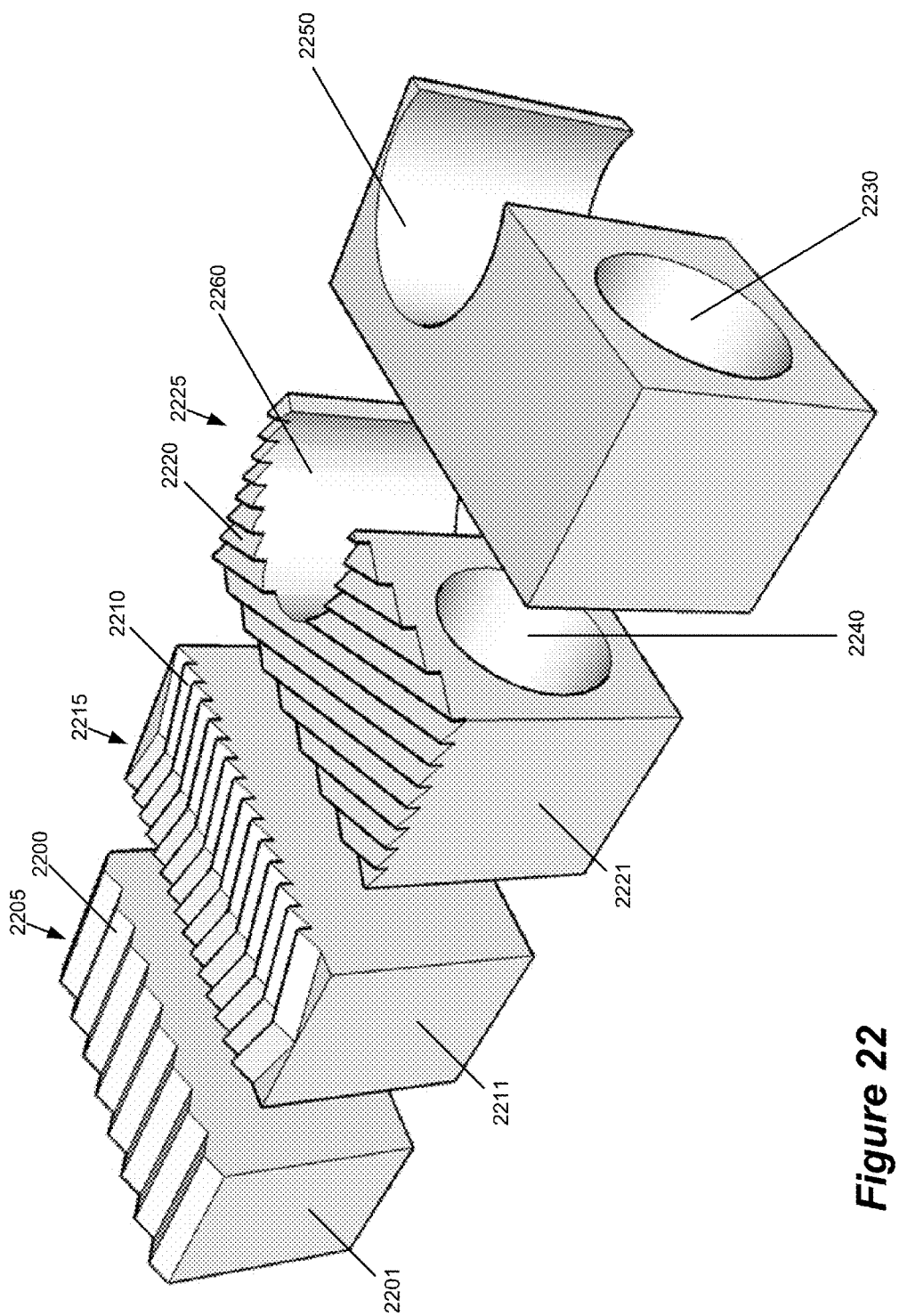
FIG. 22 depicts various fusion member surface contour features including orthogonal ridges, angled ridges, and oblique parallel ridges.

FIG. 22 depicts various fusion member surface contour features including orthogonal ridges 2200, angled ridges 2210, and oblique parallel ridges 2220. Longitudinal channels 2230 and 2240 and transverse channels 2250 and 2260 for positioning and retention of bone graft material are also illustrated.

The orthogonal ridges 2200 are in parallel with each other and are also parallel with a proximal side (i.e., side facing the medical practitioner) and a distal side 2201 (i.e., side opposite to the medical practitioner) of a fusion member 2205. When viewed from the side that is perpendicular to the orthogonal ridges 2200, the contour of each of the orthogonal ridges 2200 makes an isosceles triangle in some embodiments. In other embodiments, these orthogonal ridges 2200 are backfacing ridges. That is, the triangle that the contour of each of the orthogonal ridges 2200 makes is tilted towards the proximal side of the fusion member 2205. Such contours of the orthogonal ridges 2200 in these embodiments allow the fusion member to be inserted between vertebral bodies but prevent the fusion member 2205 from being easily withdrawn from between the vertebral bodies.

As shown, each of the angled ridges 2210 is bent about the middle and away from a distal side 2211. That is, each of the angled ridges 2210 is shaped like a letter V when viewed from above the fusion member. The tip of the shape (i.e., the tip of the letter V) is pointing to the distal side 2201 of the fusion member 2215. In addition, the angled ridges 2210 are backfacing ridges. The V-shape of the ridge and the contours of the angled ridges 2210 allow the fusion member to be inserted between vertebral bodies but prevent the fusion member 2215 from being easily withdrawn from between the vertebral bodies.

The oblique parallel ridges 2220 are in parallel with each other but are angled with a distal side 2221, a proximal side, and both longitudinal sides of a fusion member 2225 as shown. The triangle that the contour of each of the orthogonal ridges 2200 makes when viewed from a side perpendicular to the ridges is tilted. Such contours prevent the fusion member 2225 from moving in a certain direction when placed between the vertebral bodies.

These surface contours and retention channels may be combined with any of the fusion member channel configurations previously described. Bone grafting channels may be of any size and position and allow for the positioning of bone grafting material between and in contact with the opposed endplates of the adjacent vertebral bodies as well as extending from one lateral face to another lateral face of the fusion member. Placement of the bone graft material in the disc space surrounding the fusion member permits the progressive solid bony fusion between the fusion member and the adjacent vertebral bodies.

While the invention has been described with reference to numerous specific details, one of ordinary skill in the art will recognize that the invention can be embodied in other specific forms without departing from the spirit of the invention. In some embodiments, the fusion apparatus may utilize anchoring members to further anchor the fusion member to the vertebral bodies. In these instances, after the anchoring members are advanced into the marrow space of the vertebral bodies, hardening material (e.g., PMMA, bone cement, or other hardening polymer) may be injected through the anchoring members into the vertebral bodies to provide solid bony fusion between the fusion apparatus and the vertebral bodies.

I claim:

1. A fusion device system comprising:
   a fusion member, including a proximal-most end and a distal-most end, configured to position between two vertebral bodies, the fusion member comprising a channel and an indentation at the distal-most end of the fusion member; and
   a delivery member configured to traverse the channel from the proximal-most end to the distal-most end of the fusion member in order to couple to the fusion member while delivering the fusion member between the two vertebral bodies, the delivery member comprising a permanently affixed tooth for rotatably coupling with the indentation at the distal-most end of the fusion member, wherein a diameter of the indentation and a length of the tooth varies along a direction of rotation in order to ensure that the tooth and indentation unlock in only one direction of rotation.

2. The fusion device system of claim 1, wherein the tooth is a first tooth and the delivery member further comprises a second tooth, wherein the indentation is a first indentation and the fusion member further comprises a second indentation at the proximal-most end of the fusion member for rotatably receiving the second tooth when the first tooth is rotatably coupled with the first indentation.

3. The fusion device system of claim 1, wherein decoupling of the tooth from the indentation allows the delivery member to decouple from the fusion member, in order to allow the delivery member to be retracted from a patient while leaving the fusion member between the vertebral bodies.

4. The fusion device system of claim 1, wherein the indentation comprises at least one protruding tip that abuts a side of the tooth of the delivery member for preventing the delivery member from rotating more than a certain degree.

5. The fusion device system of claim 1, wherein the delivery member further comprises (i) a rod from which the delivery member's tooth protrudes and (ii) a handle coupled to the rod.

6. The fusion device system of claim 5, wherein the tooth is affixed to a portion of a surface of the rod that is less than half of a circumference of the rod along a direction of rotation of the rod.

7. The fusion device system of claim 5, wherein a portion of the rod comprising the tooth has a diameter that is greater than the diameter of another part of the rod adjacent to the tooth.

8. The fusion device system of claim 5, wherein the channel of the fusion member has a distal-most end to receive a distal-most end of the rod, wherein the two ends have matching shapes in order to facilitate rotation of the delivery member.

9. The fusion device system of claim 1, wherein the fusion member further comprises a bone-graft channel to be packed with a bone graft for enhancing solid bony fusion of the two vertebral bodies.

10. The fusion device system of claim 9, wherein the bone graft comprises a channel for the delivery member to traverse when the bone-graft channel of the fusion member is packed with the bone graft.

11. The fusion device system of claim 10, wherein channel of the bone graft is for being packed with another bone graft after the delivery member is retracted from the channel of the fusion member.

12. The fusion device system of claim 1, wherein the fusion member comprises surface contours, the contours configured (i) to allow the fusion member to be inserted between the vertebral bodies and (ii) to prevent the fusion member from being easily withdrawn from between the vertebral bodies.

13. The fusion device system of claim 1, wherein the fusion member and the delivery member are pre-assembled to form the fusion device.

14. A fusion device system comprising:
a fusion member, having proximal-most and distal-most ends, configured to position between two vertebral bodies, the fusion member comprising a channel with (i) a first groove at the proximal-most end, (ii) a second groove at a distal-most end, and (iii) a well at the distal-most end; and
a delivery member configured to enter the channel of the fusion member through the proximal-most end in order to deliver and position the fusion member between the two vertebral bodies, the delivery member comprising a rod with (i) a protrusion on a distal-most end of the rod configured to fit into the well at the distal-most end of the fusion member and (ii) permanently affixed protruding first and second teeth configured to controllably couple with the first and second grooves, respectively, in order to controllably hold the fusion member while delivering and positioning the fusion member.

15. The fusion device system of claim 14, wherein the first and second teeth are configured to rotatably couple to the first and second grooves.

16. The fusion device system of claim 14, wherein the fusion member and the delivery member are pre-assembled to form the fusion device.

17. The fusion device system of claim 14, wherein at least one side of each tooth is rounded.

18. The fusion device system of claim 14, wherein the protrusion on the distal end of the delivery member is configured to prevent lateral movement of the delivery member while coupling the first and second grooves with the first and second teeth.

19. A fusion device system comprising:
a fusion member, including a proximal-most end and a distal-most end, configured to position between two vertebral bodies, the fusion member comprising a channel and an indentation at the distal-most end of the fusion member, wherein a width of the indentation is tapered; and
a delivery member configured to traverse the channel from the proximal-most end to the distal-most end of the fusion member in order to couple to the fusion member while delivering the fusion member between the two vertebral bodies, the delivery member comprising a permanently affixed tooth for rotatably coupling with the indentation at the distal-most end of the fusion member, wherein a depth of the tooth is tapered to fit the tapered indentation, wherein the indentation comprise at least one protruding tip for preventing the delivery member from rotating more than a certain degree.

20. The fusion device system of claim 19, wherein the width of the indentation is tapered in a direction that points away from the channel.

21. The fusion device system of claim 19, wherein the width of the indentation is tapered in a direction that points towards the channel.

22. The fusion device system of claim 19, wherein decoupling of the tooth from the indentation allows the delivery member to decouple from the fusion member, in order to allow the delivery member to be retracted from a patient while leaving the fusion member between the vertebral bodies.

* * * * *